(12) United States Patent
Gray et al.

(10) Patent No.: US 11,998,448 B2
(45) Date of Patent: Jun. 4, 2024

(54) INTRAVASCULAR INTRODUCER DEVICES

(71) Applicant: Edwards Lifesciences Corporation, Irvine, CA (US)

(72) Inventors: Brian C. Gray, Trabuco Canyon, CA (US); Tung T. Le, Costa Mesa, CA (US); Andrew Oien, Mission Viejo, CA (US); Sonny Tran, Westminster, CA (US); Thanh Huy Le, Oceanside, CA (US); Robert Bowes, Trabuco Canyon, CA (US); Maria L. Saravia, Irvine, CA (US); Uy D. Trinh, Garden Grove, CA (US); Hamid Rafi, Irvine, CA (US); Alejandro J. Froimovich Rosenberg, Sherman Oaks, CA (US)

(73) Assignee: EDWARDS LIFESCIENCES CORPORATION, Irvine, CA (US)

( * ) Notice: Subject to any disclaimer, the term of this patent is extended or adjusted under 35 U.S.C. 154(b) by 215 days.

(21) Appl. No.: 17/479,225

(22) Filed: Sep. 20, 2021

(65) Prior Publication Data

US 2022/0000618 A1 Jan. 6, 2022

Related U.S. Application Data

(60) Continuation of application No. 16/208,457, filed on Dec. 3, 2018, now Pat. No. 11,123,188, which is a (Continued)

(51) Int. Cl.
*A61F 2/24* (2006.01)
*A61F 2/95* (2013.01)

(52) U.S. Cl.
CPC .......... *A61F 2/2436* (2013.01); *A61F 2/9517* (2020.05)

(58) Field of Classification Search
CPC ............................. A61F 2/2436; A61F 2/9517
See application file for complete search history.

(56) References Cited

U.S. PATENT DOCUMENTS

| 3,365,728 A | 1/1968 | Edwards et al. |
| 3,725,961 A | 4/1973 | Magovern et al. |
| (Continued) | | |

FOREIGN PATENT DOCUMENTS

| AU | 2002212418 B2 | 3/2006 |
| DE | 19532846 A1 | 3/1997 |
| (Continued) | | |

OTHER PUBLICATIONS

International Search Report from corresponding PCT case No. PCT/US2015/027764 dated Aug. 13, 2015.

*Primary Examiner* — Phong Son H Dang
(74) *Attorney, Agent, or Firm* — Klarquist Sparkman, LLP; Joel B. German

(57) ABSTRACT

Disclosed embodiments of introducer devices provide hemostatic sealing and allow a delivery catheter to be inserted through the introducer seals without the use of a separate loader device that covers a medical device that is mounted on the catheter. Some disclosed introducers comprise a housing, a distal sheath extending distally from the housing and adapted to be inserted into a patient's vasculature, a distal hemostatic seal mounted within the housing and a proximal hemostatic seal mounted within the housing, and a slidable tube positioned within the housing that is movable longitudinally relative to the distal hemostatic seal between a proximal position and a distal position, wherein in the proximal position a distal end of the tube is positioned proximal to the distal hemostatic seal with the distal hemostatic seal closed, and wherein in the distal position the distal end of the tube extends through the distal hemostatic seal.

15 Claims, 19 Drawing Sheets

Related U.S. Application Data division of application No. 14/695,607, filed on Apr. 24, 2015, now Pat. No. 10,154,904.

(60) Provisional application No. 61/985,330, filed on Apr. 28, 2014.

(56) References Cited

U.S. PATENT DOCUMENTS

| | | | |
|---|---|---|---|
| 3,983,581 | A | 10/1976 | Angell et al. |
| 4,035,849 | A | 7/1977 | Angell et al. |
| 4,592,340 | A | 6/1986 | Boyles |
| 4,781,702 | A * | 11/1988 | Herrli ............... A61M 39/14 604/905 |
| 4,935,010 | A * | 6/1990 | Cox ............... A61M 39/045 604/167.03 |
| 4,994,077 | A | 2/1991 | Dobben |
| 5,059,177 | A | 10/1991 | Towne et al. |
| 5,114,408 | A * | 5/1992 | Fleischhaker ..... A61M 39/0606 604/905 |
| 5,258,023 | A | 11/1993 | Reger |
| 5,350,393 | A * | 9/1994 | Yoon ............. A61B 17/3496 604/164.12 |
| 5,376,077 | A | 12/1994 | Gomringer |
| 5,411,552 | A | 5/1995 | Andersen et al. |
| 5,458,640 | A | 10/1995 | Gerrone |
| 5,476,506 | A | 12/1995 | Lunn |
| 5,554,185 | A | 9/1996 | Block et al. |
| 5,591,195 | A | 1/1997 | Taheri et al. |
| 5,599,305 | A | 2/1997 | Hermann et al. |
| 5,628,786 | A | 5/1997 | Banas et al. |
| 5,639,274 | A | 6/1997 | Fischell et al. |
| 5,693,088 | A | 12/1997 | Lazarus |
| 5,728,068 | A | 3/1998 | Leone et al. |
| 5,755,783 | A | 5/1998 | Stobie et al. |
| 5,769,882 | A | 6/1998 | Fogarty et al. |
| 5,776,188 | A | 7/1998 | Shepherd et al. |
| 5,840,081 | A | 11/1998 | Andersen et al. |
| 5,843,161 | A | 12/1998 | Solovay |
| 5,843,179 | A | 12/1998 | Vanney et al. |
| 5,855,601 | A | 1/1999 | Bessler et al. |
| 5,911,710 | A | 6/1999 | Barry et al. |
| 5,957,949 | A | 9/1999 | Leonhardt et al. |
| 5,968,068 | A | 10/1999 | Dehdashtian et al. |
| 6,015,431 | A | 1/2000 | Thornton et al. |
| 6,110,198 | A | 8/2000 | Fogarty et al. |
| 6,168,614 | B1 | 1/2001 | Andersen et al. |
| 6,197,042 | B1 * | 3/2001 | Ginn ................ A61B 17/128 606/139 |
| 6,206,911 | B1 | 3/2001 | Milo |
| 6,217,585 | B1 | 4/2001 | Houser et al. |
| 6,306,164 | B1 | 10/2001 | Kujawski |
| 6,352,554 | B2 | 3/2002 | De Paulis |
| 6,379,372 | B1 | 4/2002 | Dehdashtian et al. |
| 6,454,799 | B1 | 9/2002 | Schreck |
| 6,458,153 | B1 | 10/2002 | Bailey et al. |
| 6,461,382 | B1 | 10/2002 | Cao |
| 6,482,228 | B1 | 11/2002 | Norred |
| 6,527,979 | B2 | 3/2003 | Constantz |
| 6,540,782 | B1 | 4/2003 | Snyders |
| 6,582,462 | B1 | 6/2003 | Andersen et al. |
| 6,652,578 | B2 | 11/2003 | Bailey et al. |
| 6,663,667 | B2 | 12/2003 | Dehdashtian et al. |
| 6,729,356 | B1 | 5/2004 | Baker et al. |
| 6,730,118 | B2 | 5/2004 | Spenser et al. |
| 6,733,525 | B2 | 5/2004 | Yang et al. |
| 6,767,362 | B2 | 7/2004 | Schreck |
| 6,773,456 | B1 | 8/2004 | Gordon et al. |
| 6,814,754 | B2 | 11/2004 | Greenhalgh |
| 6,830,584 | B1 | 12/2004 | Seguin |
| 6,846,325 | B2 | 1/2005 | Liddicoat |
| 6,893,460 | B2 | 5/2005 | Spenser et al. |
| 6,904,909 | B2 | 6/2005 | Andreas et al. |
| 6,908,481 | B2 | 6/2005 | Cribier |
| 6,911,040 | B2 | 6/2005 | Johnson et al. |
| 7,018,406 | B2 | 3/2006 | Seguin et al. |
| 7,018,408 | B2 | 3/2006 | Bailey et al. |
| 7,101,353 | B2 * | 9/2006 | Lui ................... A61M 39/0606 604/164.05 |
| 7,101,396 | B2 | 9/2006 | Artof et al. |
| 7,147,663 | B1 | 12/2006 | Berg et al. |
| 7,175,652 | B2 | 2/2007 | Cook et al. |
| 7,192,441 | B2 | 3/2007 | Sherry |
| 7,264,632 | B2 | 9/2007 | Wright et al. |
| 7,276,084 | B2 | 10/2007 | Yang et al. |
| 7,318,278 | B2 | 1/2008 | Zhang et al. |
| 7,374,571 | B2 | 5/2008 | Pease et al. |
| 7,390,317 | B2 * | 6/2008 | Taylor ................ A61B 17/3498 606/167 |
| 7,393,360 | B2 | 7/2008 | Spenser et al. |
| 7,510,575 | B2 | 3/2009 | Spenser et al. |
| 7,585,321 | B2 | 9/2009 | Cribier |
| 7,618,446 | B2 | 11/2009 | Andersen et al. |
| 7,731,742 | B2 | 6/2010 | Schlick et al. |
| 7,736,339 | B2 * | 6/2010 | Woehr ............. A61M 25/0097 604/110 |
| 7,780,725 | B2 | 8/2010 | Haug et al. |
| 7,785,366 | B2 | 8/2010 | Maurer et al. |
| 7,959,661 | B2 | 6/2011 | Hijlkema et al. |
| 7,981,092 | B2 * | 7/2011 | Duke ................. A61B 17/3462 604/264 |
| 8,029,556 | B2 | 10/2011 | Rowe |
| 8,105,377 | B2 | 1/2012 | Liddicoat |
| 8,128,681 | B2 | 3/2012 | Shoemaker et al. |
| 8,167,932 | B2 | 5/2012 | Bourang |
| 8,192,405 | B2 * | 6/2012 | Racenet ................ A61B 17/34 604/167.03 |
| 8,262,671 | B2 * | 9/2012 | Osypka ............. A61M 25/0097 606/1 |
| 8,308,691 | B2 * | 11/2012 | Woehr ............. A61B 5/150992 604/167.03 |
| 8,425,593 | B2 | 4/2013 | Braido et al. |
| 8,430,851 | B2 * | 4/2013 | McGinley ........... A61M 13/003 604/167.03 |
| 8,430,925 | B2 | 4/2013 | Forster et al. |
| 8,449,606 | B2 | 5/2013 | Eliasen et al. |
| 8,628,056 | B2 * | 1/2014 | LaBean ................ B65D 51/002 604/167.04 |
| 8,636,686 | B2 * | 1/2014 | Minnelli ............. A61B 17/3474 604/167.03 |
| 8,652,104 | B2 * | 2/2014 | Goral ............. A61M 25/0014 604/164.01 |
| 8,679,090 | B2 * | 3/2014 | Anderson ............. A61M 39/26 604/536 |
| 8,690,831 | B2 * | 4/2014 | Duke ................. A61B 17/3462 604/23 |
| 8,721,717 | B2 | 5/2014 | Shoemaker et al. |
| 8,795,357 | B2 | 8/2014 | Yohanan et al. |
| 8,808,356 | B2 | 8/2014 | Braido et al. |
| 8,845,721 | B2 | 9/2014 | Braido et al. |
| 8,979,922 | B2 | 3/2015 | Jayasinghe et al. |
| 8,992,608 | B2 | 3/2015 | Haug et al. |
| 9,220,594 | B2 | 12/2015 | Braido et al. |
| 9,241,794 | B2 | 1/2016 | Braido et al. |
| 9,289,296 | B2 | 3/2016 | Braido et al. |
| 9,326,856 | B2 | 5/2016 | Schraut et al. |
| 9,345,571 | B1 | 5/2016 | Braido et al. |
| 9,351,828 | B2 | 5/2016 | Braido et al. |
| 9,351,831 | B2 | 5/2016 | Braido et al. |
| 9,351,832 | B2 | 5/2016 | Braido et al. |
| 9,358,041 | B2 * | 6/2016 | Moreno, Jr. ....... A61B 17/3462 |
| 9,414,911 | B2 | 8/2016 | Braido et al. |
| 9,545,307 | B2 | 1/2017 | Braido et al. |
| 9,549,815 | B2 | 1/2017 | Braido et al. |
| 9,750,920 | B2 * | 9/2017 | Vincent ............. A61M 25/0097 |
| 2001/0021825 | A1 | 9/2001 | Becker et al. |
| 2001/0021872 | A1 | 9/2001 | Bailey et al. |
| 2001/0027338 | A1 | 10/2001 | Greenberg |
| 2001/0039450 | A1 | 11/2001 | Pavcnik et al. |
| 2002/0032481 | A1 | 3/2002 | Gabbay |
| 2002/0128604 | A1 | 9/2002 | Nakajima |
| 2003/0050694 | A1 | 3/2003 | Yang et al. |
| 2003/0074058 | A1 | 4/2003 | Sherry |

(56) References Cited

U.S. PATENT DOCUMENTS

| | | |
|---|---|---|
| 2003/0236567 A1 | 12/2003 | Elliot |
| 2004/0033364 A1 | 2/2004 | Spiridigliozzi et al. |
| 2004/0068248 A1 | 4/2004 | Mooney et al. |
| 2004/0082989 A1 | 4/2004 | Cook et al. |
| 2004/0098096 A1 | 5/2004 | Eton |
| 2004/0133263 A1 | 7/2004 | Dusbabek et al. |
| 2004/0186563 A1 | 9/2004 | Lobbi |
| 2004/0186565 A1 | 9/2004 | Schreck |
| 2004/0210304 A1 | 10/2004 | Seguin et al. |
| 2004/0260389 A1 | 12/2004 | Case et al. |
| 2005/0043790 A1 | 2/2005 | Seguin |
| 2005/0080474 A1 | 4/2005 | Andreas et al. |
| 2005/0096736 A1 | 5/2005 | Osse et al. |
| 2005/0137687 A1 | 6/2005 | Salahieh et al. |
| 2005/0203614 A1 | 9/2005 | Forster et al. |
| 2005/0203617 A1 | 9/2005 | Forster et al. |
| 2005/0212221 A1* | 9/2005 | Smith .............. A61B 17/3462 277/628 |
| 2006/0025857 A1 | 2/2006 | Bergheim et al. |
| 2007/0005131 A1 | 1/2007 | Taylor |
| 2007/0073387 A1 | 3/2007 | Forster et al. |
| 2007/0203575 A1 | 8/2007 | Forster et al. |
| 2007/0265700 A1 | 11/2007 | Eliasen et al. |
| 2008/0065011 A1 | 3/2008 | Marchand et al. |
| 2008/0125853 A1 | 5/2008 | Bailey et al. |
| 2008/0294230 A1 | 11/2008 | Parker |
| 2009/0099653 A1 | 4/2009 | Suri et al. |
| 2009/0132035 A1 | 5/2009 | Roth et al. |
| 2009/0157175 A1 | 6/2009 | Benichou |
| 2009/0276040 A1 | 11/2009 | Rowe et al. |
| 2009/0281619 A1 | 11/2009 | Le et al. |
| 2009/0319037 A1 | 12/2009 | Rowe et al. |
| 2010/0036323 A1* | 2/2010 | Smith .............. A61B 17/3498 604/167.01 |
| 2010/0049313 A1 | 2/2010 | Alon et al. |
| 2010/0168839 A1 | 7/2010 | Braido et al. |
| 2010/0198347 A1 | 8/2010 | Zakay et al. |
| 2010/0274193 A1* | 10/2010 | Patton .............. A61B 17/3462 604/167.01 |
| 2010/0298775 A1* | 11/2010 | Berry .............. A61B 17/3462 604/167.03 |
| 2011/0015729 A1 | 1/2011 | Jimenez et al. |
| 2011/0282286 A1 | 11/2011 | Argentine |
| 2012/0004613 A1* | 1/2012 | Franer .............. A61B 17/3462 604/167.03 |
| 2012/0035719 A1 | 2/2012 | Forster et al. |
| 2012/0123529 A1 | 5/2012 | Levi et al. |
| 2012/0215303 A1 | 8/2012 | Quadri et al. |
| 2012/0310166 A1 | 12/2012 | Huff |
| 2013/0218082 A1* | 8/2013 | Hyer .............. A61M 25/0097 604/256 |
| 2013/0304179 A1* | 11/2013 | Bialas .............. A61M 25/10184 623/1.11 |
| 2013/0317598 A1 | 11/2013 | Rowe et al. |
| 2013/0338765 A1 | 12/2013 | Braido et al. |
| 2014/0350663 A1 | 11/2014 | Braido et al. |
| 2015/0073541 A1 | 3/2015 | Salahieh et al. |
| 2015/0073546 A1 | 3/2015 | Braido |
| 2015/0157455 A1 | 6/2015 | Hoang et al. |
| 2015/0282932 A1 | 10/2015 | Neuman et al. |
| 2015/0343179 A1* | 12/2015 | Schumacher ..... A61M 25/0662 604/171 |
| 2016/0213466 A1 | 7/2016 | Braido et al. |
| 2016/0213468 A1 | 7/2016 | Braido et al. |
| 2016/0242904 A1 | 8/2016 | Braido et al. |
| 2017/0360560 A1* | 12/2017 | Marchand ......... A61M 25/0662 |

FOREIGN PATENT DOCUMENTS

| | | |
|---|---|---|
| DE | 19907646 A1 | 8/2000 |
| EP | 0564373 A1 | 10/1993 |
| EP | 0592410 B1 | 10/1995 |
| EP | 0850607 A1 | 7/1998 |
| EP | 0875262 A2 | 11/1998 |
| EP | 1796597 A2 | 6/2007 |
| EP | 2155114 A1 | 2/2010 |
| EP | 2299938 A2 | 3/2011 |
| EP | 2540338 A1 | 1/2013 |
| EP | 2572675 A2 | 3/2013 |
| EP | 2572676 A2 | 3/2013 |
| EP | 2698129 A1 | 2/2014 |
| EP | 2745805 A1 | 6/2014 |
| EP | 2749254 A1 | 7/2014 |
| EP | 2815723 A1 | 12/2014 |
| EP | 2815724 A1 | 12/2014 |
| EP | 2815725 A1 | 12/2014 |
| EP | 2926766 A1 | 10/2015 |
| EP | 2967851 A2 | 1/2016 |
| EP | 3025680 A1 | 6/2016 |
| EP | 3025681 A1 | 6/2016 |
| EP | 3028670 A1 | 6/2016 |
| EP | 3028671 A1 | 6/2016 |
| FR | 2815844 A1 | 5/2002 |
| JP | H10179757 A | 7/1998 |
| JP | H114894 A | 1/1999 |
| JP | 2002505920 A | 2/2002 |
| JP | 2009530070 A | 8/2009 |
| JP | 2011004894 A | 1/2011 |
| WO | 9117720 | 11/1991 |
| WO | 9748350 A1 | 12/1997 |
| WO | 9829057 A1 | 7/1998 |
| WO | 0044313 A1 | 8/2000 |
| WO | 0106959 A1 | 2/2001 |
| WO | 0149213 A2 | 7/2001 |
| WO | 0154625 A1 | 8/2001 |
| WO | 0170308 A1 | 9/2001 |
| WO | 0176510 A2 | 10/2001 |
| WO | 0219951 A1 | 3/2002 |
| WO | 0222054 A1 | 3/2002 |
| WO | 0236048 A1 | 5/2002 |
| WO | 0247575 A2 | 6/2002 |
| WO | 03003949 A2 | 1/2003 |
| WO | 03037222 A2 | 5/2003 |
| WO | 03047468 A1 | 6/2003 |
| WO | 03088873 A1 | 10/2003 |
| WO | 03096932 A1 | 11/2003 |
| WO | 2005084595 A1 | 9/2005 |
| WO | 2006005015 A2 | 1/2006 |
| WO | 2006032051 A2 | 3/2006 |
| WO | 2006111391 A1 | 10/2006 |
| WO | 2006138173 A2 | 12/2006 |
| WO | 2005102015 A3 | 4/2007 |
| WO | 2007047488 A2 | 4/2007 |
| WO | 2007067942 A1 | 6/2007 |
| WO | 2009042196 A2 | 4/2009 |
| WO | 2010121076 A2 | 10/2010 |

* cited by examiner

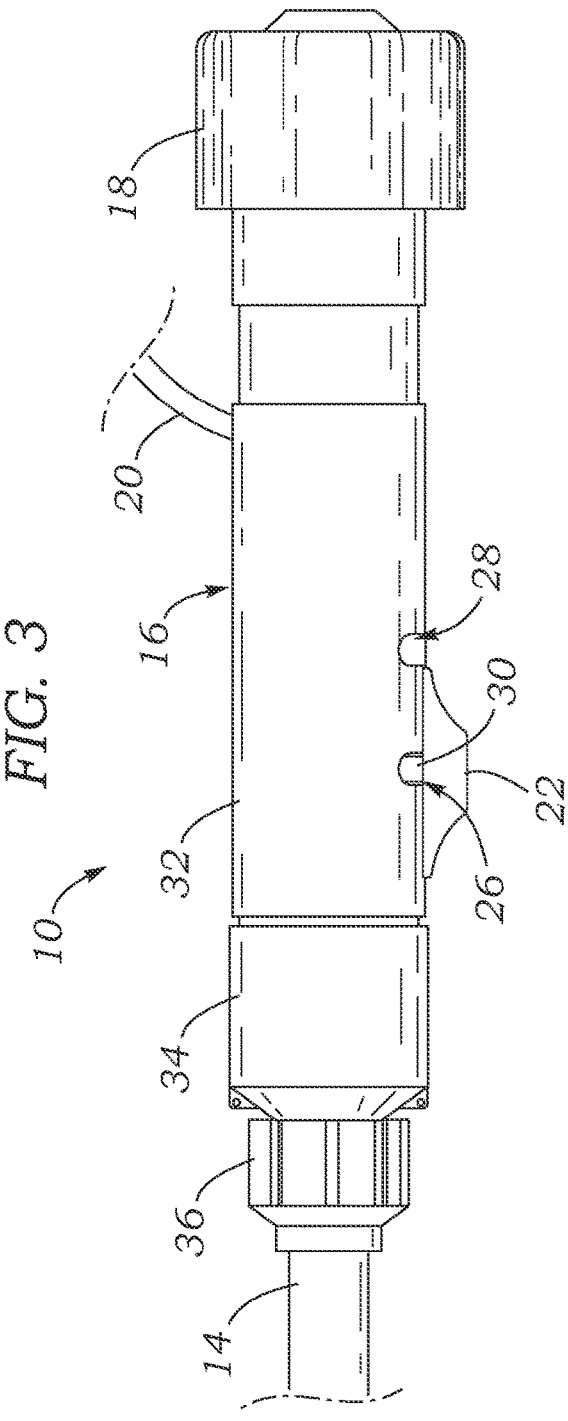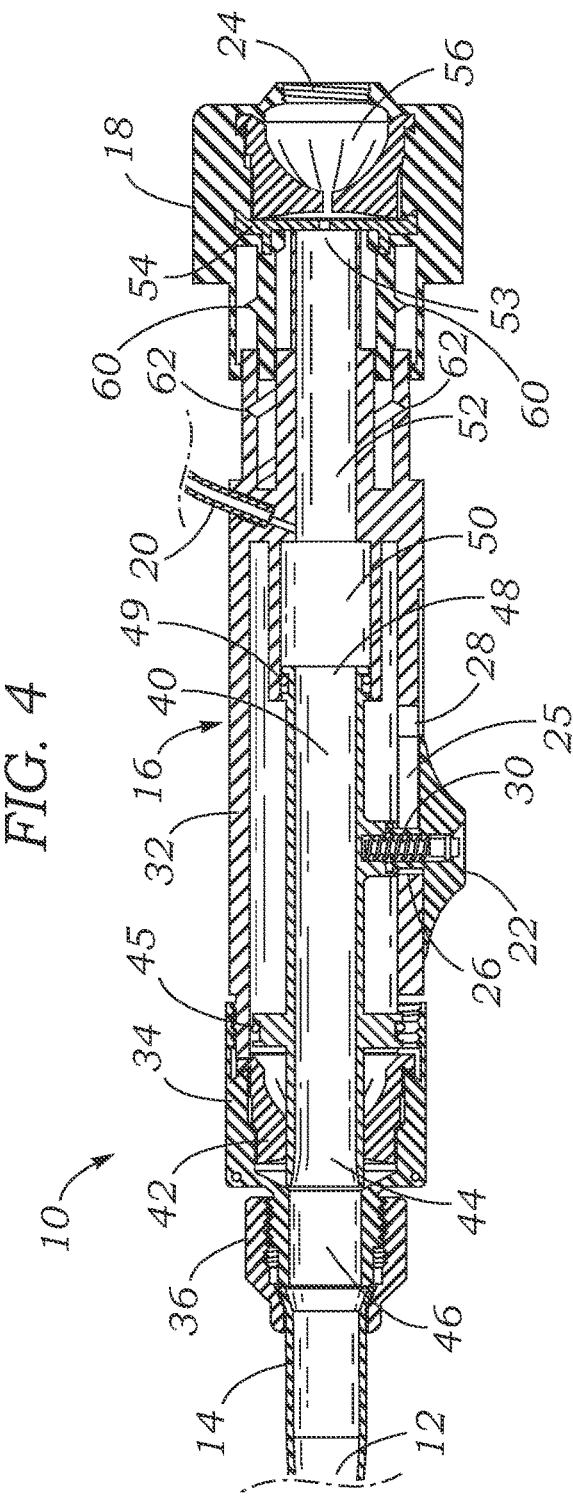

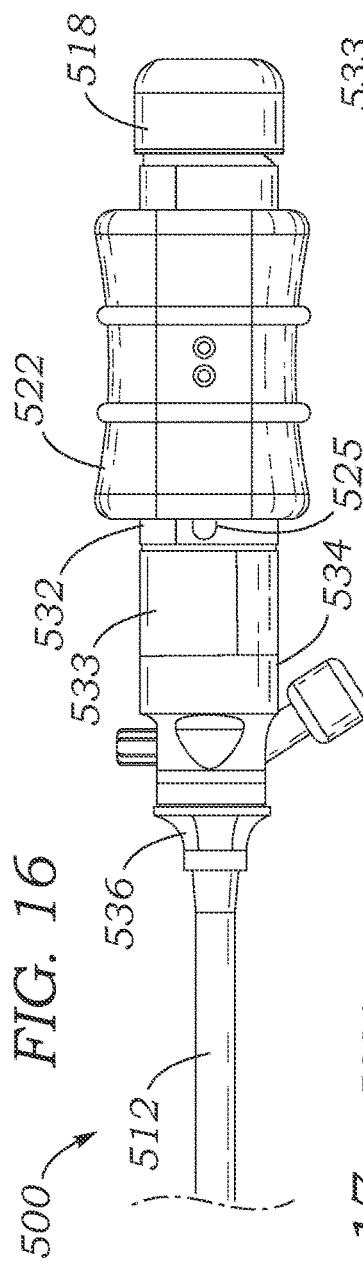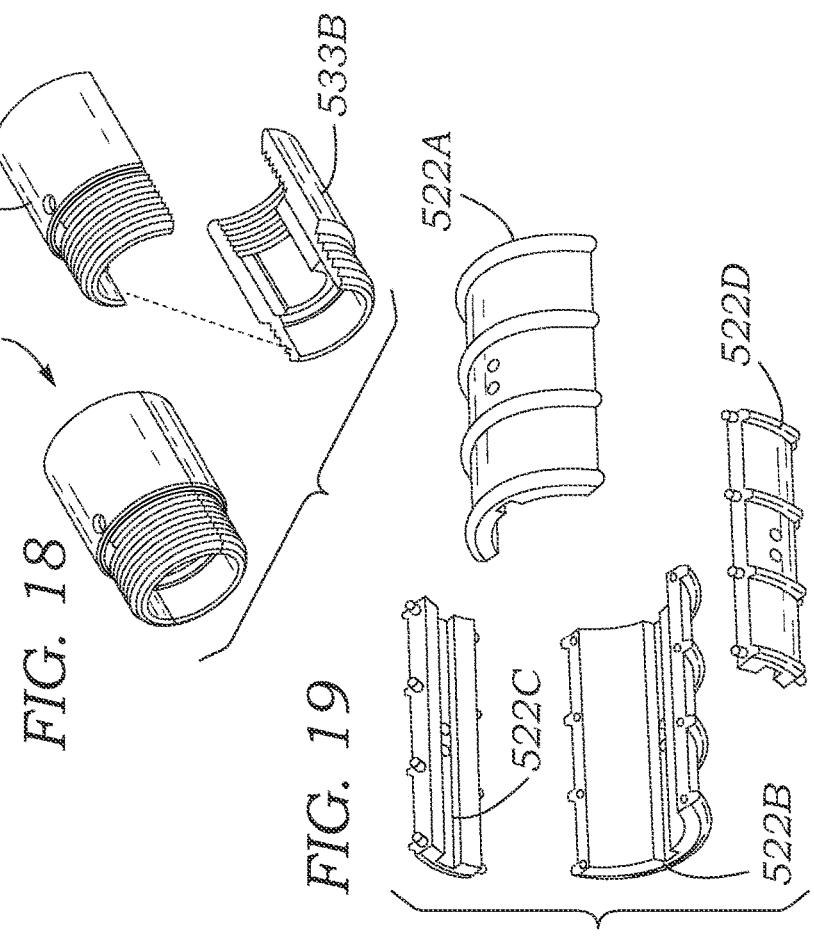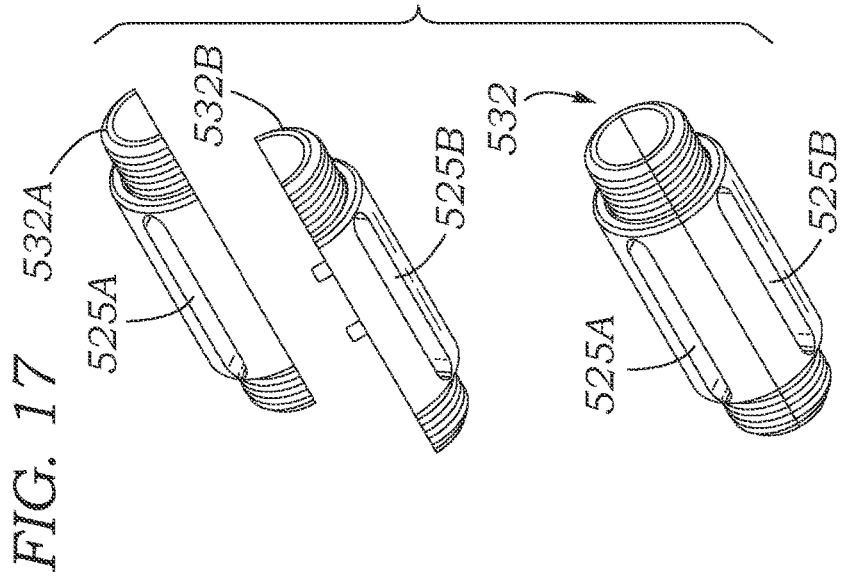

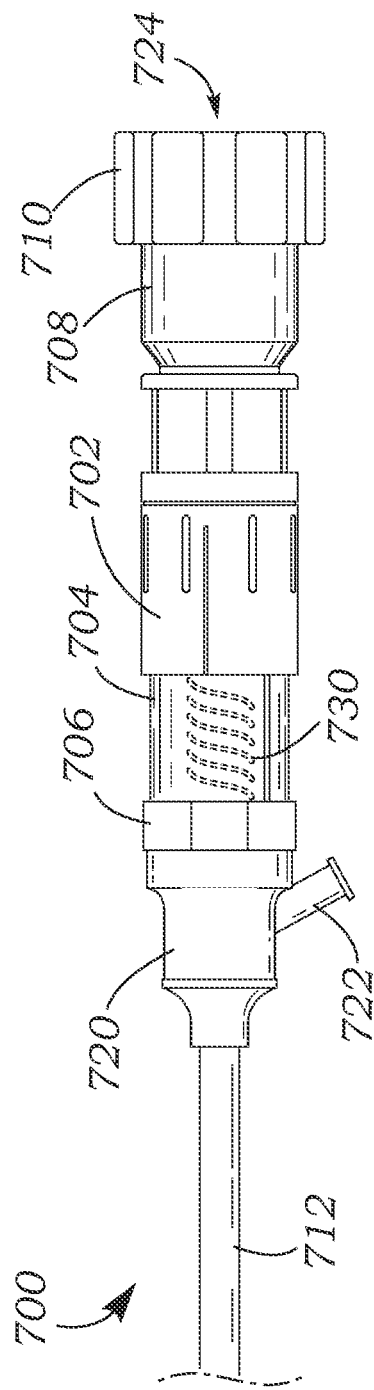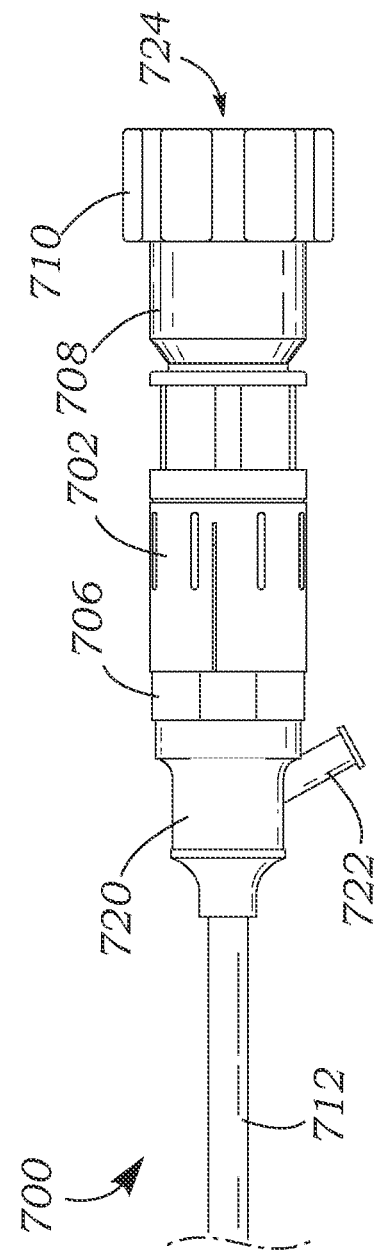
FIG. 24
FIG. 25

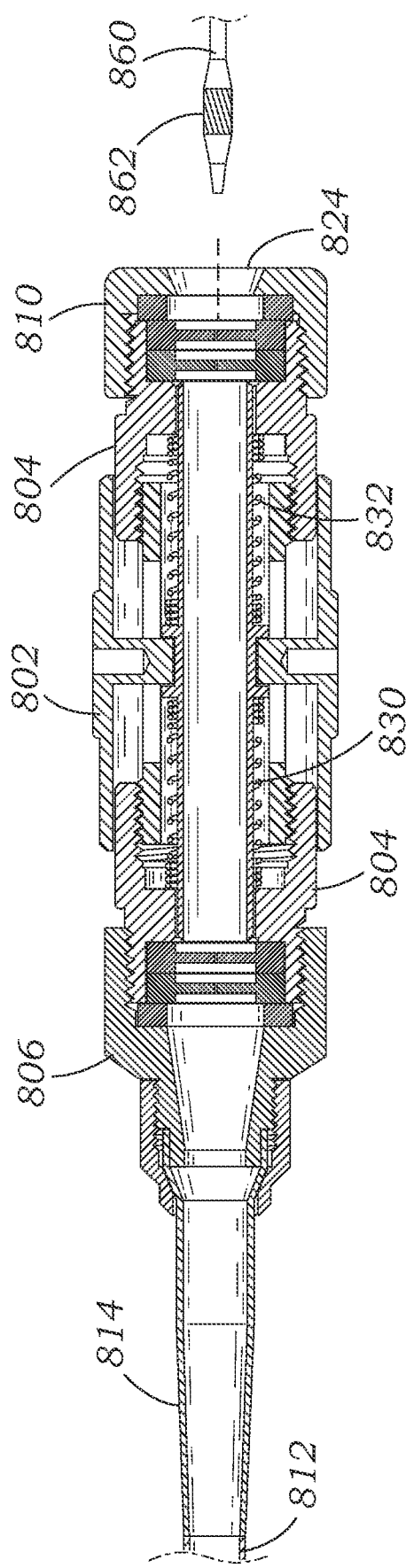

INTRAVASCULAR INTRODUCER DEVICES

CROSS-REFERENCE TO RELATED APPLICATIONS

This application is a continuation of U.S. patent application Ser. No. 16/208,457, filed Dec. 3, 2018, which is a divisional of U.S. patent application Ser. No. 14/695,607, filed Apr. 24, 2015, now U.S. Pat. No. 10,154,904, which claims the benefit of U.S. Provisional Patent Application No. 61/985,330, filed Apr. 28, 2014, all of which are incorporated by reference herein in their entirety.

FIELD

This application is related to devices for introducing a catheter or other device into a patient's vasculature, such as for delivering a medical device into the body.

BACKGROUND

A conventional method of introducing a transcatheter prosthetic heart valve into a patient's vasculature and toward the heart includes using a conventional introducer device to create an access port through the skin to a vein, and using a separate loader device to load a delivery catheter, with a crimped prosthetic heart valve mounted thereon, into and through the introducer device into the vasculature. The loader device typically covers the crimped heart valve with a sheath to protect it while the delivery catheter is passed through hemostatic seals in the introducer device. Covering the crimped prosthetic heart valve can reduce the risk of the crimped prosthetic heart valve migrating relative delivery catheter and can reduce the risk of the crimped prosthetic heart valve being damaged when it passes through the seals of the introducer device.

SUMMARY

Disclosed herein are embodiments of introducer devices that provide hemostatic sealing and allow a delivery catheter to be inserted into and retrieved from a patient's vasculature. A delivery catheter can be passed through the device's seals without the use of a separate loader device that covers a medical device, such as a crimped prosthetic heart valve, that is mounted on the delivery catheter.

Some disclosed introducer devices comprise a housing, a distal sheath extending distally from the housing and adapted to be inserted into a patient's vasculature with the housing positioned outside of the patient's vasculature, a distal hemostatic seal mounted within the housing and a proximal hemostatic seal mounted within the housing, and a shuttle or tube positioned within the housing that is movable longitudinally relative to the distal hemostatic seal and the housing between a proximal position and a distal position, wherein in the proximal position a distal end of the tube is positioned proximal to the distal hemostatic seal with the distal hemostatic seal closed, and wherein in the distal position the distal end of the tube extends through the distal hemostatic seal.

In some embodiments, when the tube is in the distal position, a proximal end of the tube is positioned distal to the proximal hemostatic seal and the proximal hemostatic seal is closed, and when the tube is in the proximal position, the proximal end of the tube extends through the proximal hemostatic seal.

In other embodiments, the introducer includes a second tube, such as a fixed part of the housing, and the proximal hemostatic seal is movable longitudinally relative to a proximal end of the second tube between a distal position wherein the second tube extends through the proximal hemostatic seal and a proximal position wherein the proximal hemostatic seal is closed and positioned proximal to the second tube. In such embodiments, the housing can comprise a main housing and a proximal end portion that are movable longitudinally relative to each other, and the proximal hemostatic seal is mounted within the proximal end portion while the second tube is part of the main housing.

The tube that opens the distal seal can be part of a shuttle that is slidable relative to the housing and the distal seal. The shuttle can also include an actuator that extends radially through the housing and forms a handle or grip on the outside for a user to manipulate. In some embodiments, the shuttle actuator can slide along a slot in the housing, and the slot can be configured to allow the shuttle to be locking in the distal or proximal position by twisting the shuttle actuator relative to the housing.

When the proximal seal is opened, a delivery catheter can be inserted through a proximal port in the device and into the tube between the seals without the delivery catheter contacting the proximal seal. Then, the tube can be moved to the distal position to allow the delivery catheter to be advanced distally from the tube into the distal sheath without contacting the distal hemostatic seal. After the medical device carried on the delivery catheter is advanced through the introducer, the seals can hemostatically seal around the proximal portions of the catheter while a procedure occurs.

In some embodiments, the process can be generally reversed to allow the delivery catheter with a medical device still mounted thereon to be retrieved back proximally out of the body through the introducer without the seals of the introducer damaging or dislodging the medical device as is passed through the introducer. The seals are consequently also protected from being damaged by the medical device mounted on the catheter. Because the delivery system and the seals are protected from damage by the tube or tubes during retrieval, the same delivery system can subsequently be re-introduced into the body using the same introducer, with minimized risk of malfunction.

In some embodiments, the distal and/or proximal seal can comprise a narrow guidewire passageway adapted to hemostatically seal around a guidewire extending through the seal, and can comprise a flap or flaps covering the guidewire passageway and adapted to hemostatically seal when nothing is extending through the seal.

The foregoing and other objects, features, and advantages of the disclosed technology will become more apparent from the following detailed description, which proceeds with reference to the accompanying figures.

BRIEF DESCRIPTION OF THE DRAWINGS

FIG. 3 is a side view of a proximal portion of the device of FIG. 1, with a shuttle in a distal position and an end hub in a proximal position.

FIG. 4 is a cross-sectional view of FIG. 3.

FIG. 16 is a side view of another exemplary introducer device having longitudinally split components.

FIGS. 17-19 show longitudinally split components of the device of FIG. 16.

FIG. 24 is a side view of another exemplary embodiment of an introducer device, in an elongated configuration.

FIG. 25 is a side view of the device of FIG. 24, in a shortened configuration.

FIG. 28 is a cross-sectional view of the device of FIG. 26, with a delivery catheter ready to be inserted.

FIG. 29 is a cross-sectional view of the device of FIG. 26, with a proximal seal opened and the delivery catheter inserted through the proximal seal.

DETAILED DESCRIPTION

Figure 1:
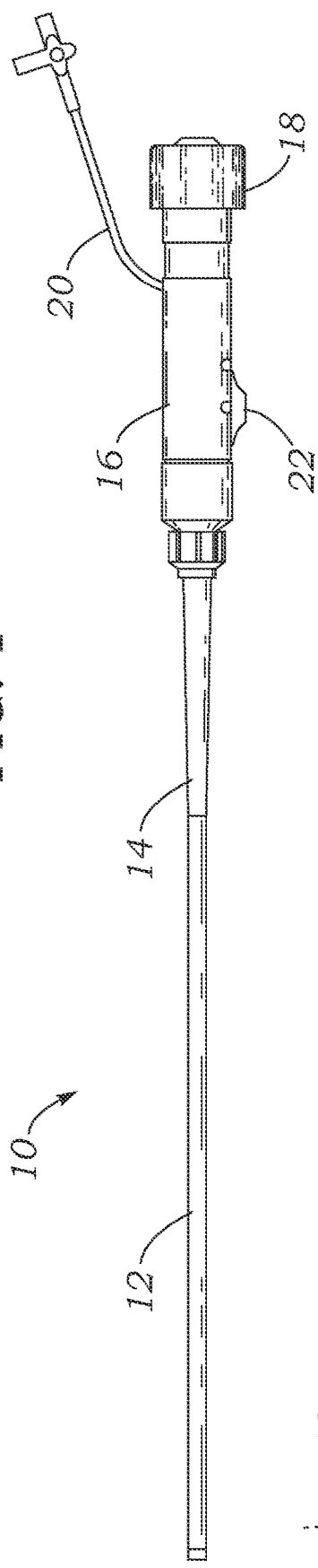
FIG. 1 is a side view of an exemplary introducer device.

FIGS. 1-6 show an exemplary introducer 10 that provides hemostatic sealing and allows a delivery catheter to be inserted through the introducer and into a patient's vasculature without the use of a separate loader device. The introducer 10 can comprise a distal sheath 12 that is inserted through the skin into a vessel, a tapered transition sheath 14, a housing 16, a proximal hub 18, a flush port 20, and a longitudinally slidable shuttle 22. The housing 16 supports a distal hemostatic seal 42, and the hub 18 supports a proximal hemostatic seal 56 (see FIGS. 4-6). The introducer 10 can be manipulated to selectively open and close the seals 42, 56 to allow a delivery catheter (not shown) to be inserted distally through the introducer into the body and/or retracted proximally through the introducer without damaging a device mounted onto the delivery catheter. For example, a delivery catheter can include a crimped prosthetic heart valve, a crimped stent, an inflatable balloon, and/or other medical devices mounted on the catheter near the distal end of the catheter for deployment into a patient's vasculature. Such various devices that can be mounted on a delivery catheter are referred to herein generally as "medical devices" and together with the delivery catheter as a "delivery system."

The housing 16 can comprise a main housing 32, a distal seal housing 34, and/or a distal sheath housing 36, as best shown in FIG. 3. As best shown in FIG. 4, the distal seal housing 34 can be secured to the distal end of the main housing 32 via a threaded engagement, and the distal sheath housing 36 can be secured to the distal end of the seal housing 34 via a threaded engagement. The distal seal 42 is mounted within the distal seal housing 34, and the distal sheath 12 and the transition sheath 14 are secured at their proximal ends by the distal sheath housing 36.

Figure 5:
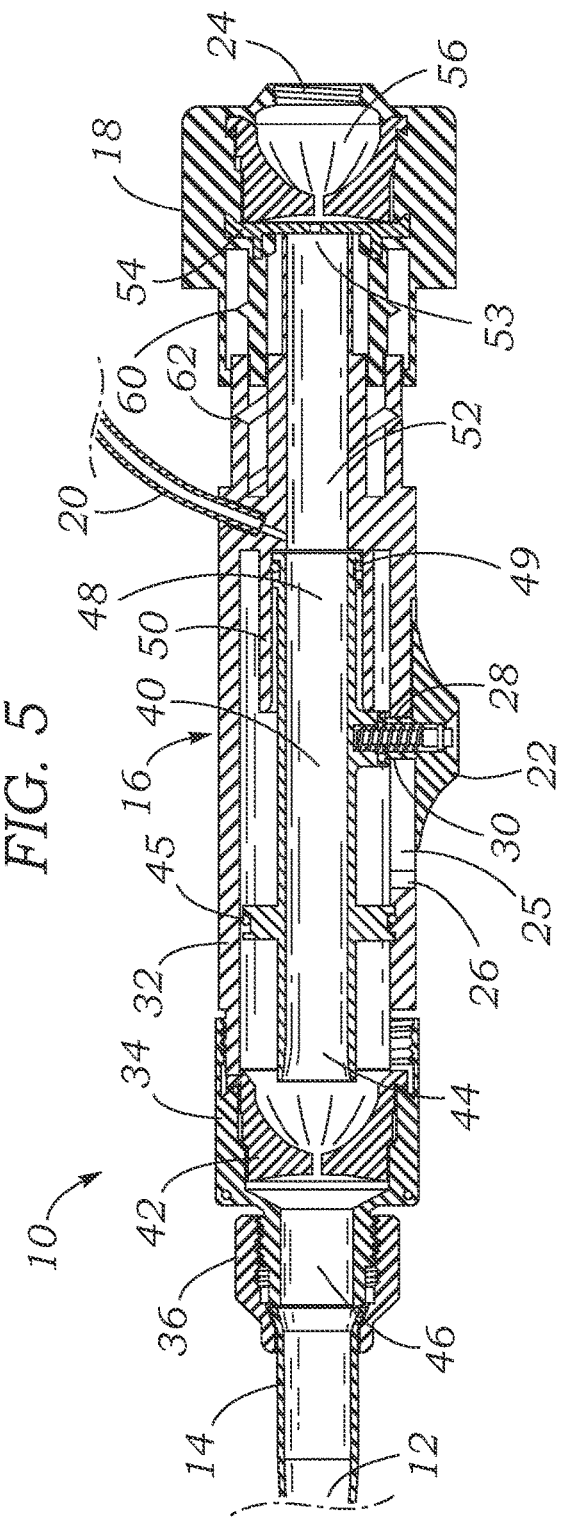
FIG. 5 is a cross-sectional view of the proximal portion of the device of FIG. 1, with the shuttle in a proximal position and the end hub in the proximal position.
Figure 6:
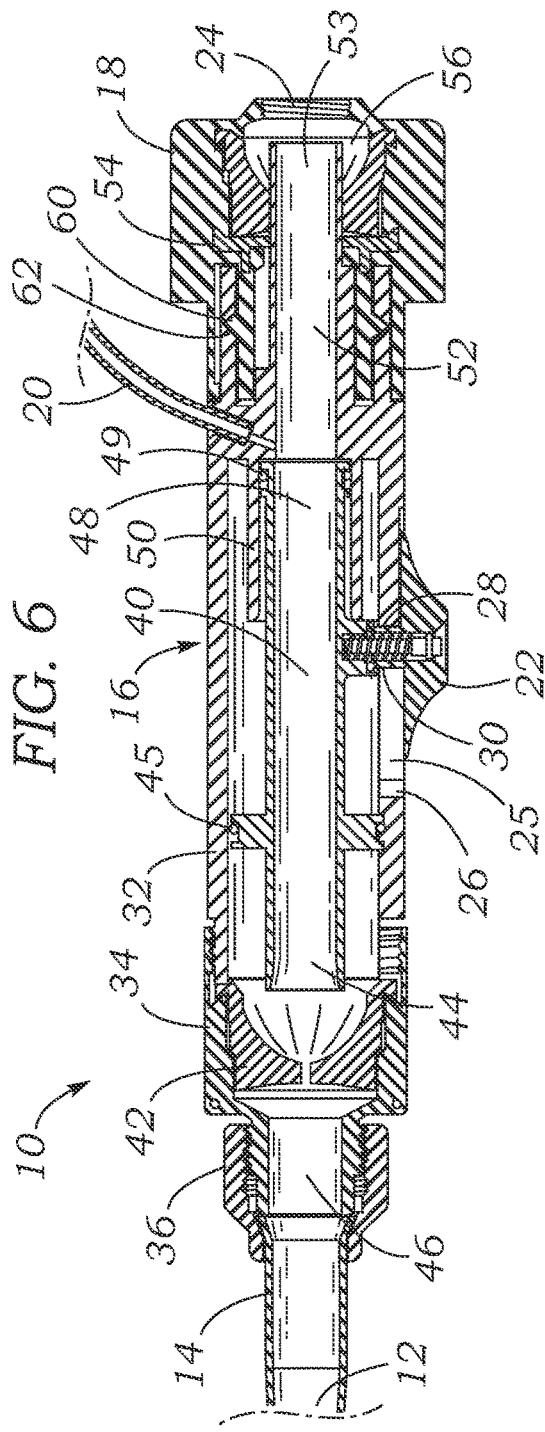
FIG. 6 is a cross-sectional view of the proximal portion of the device of FIG. 1, with the shuttle in the proximal position and the end hub in a distal position.

The main housing 32 houses the shuttle 22 such that the shuttle 22 can slide longitudinally relative to the housing 16 between a distal position (FIGS. 1-4) and a proximal position (FIGS. 5-6). The shuttle 22 can comprise a longitudinal shuttle sheath 40 that has a distal end 44 and a proximal end 48. The distal end 44 of the shuttle sheath 40 is positioned proximal to the distal seal 42 when the shuttle is in the proximal position (FIGS. 5-6) and moves through the distal seal 42 when the shuttle is in the distal position (FIG. 4). The proximal end 48 of the shuttle sheath can slide telescopically within a larger diameter section 50 of the main housing 32 with a sealing engagement therebetween, such as with an O-ring type seal 49. The shuttle sheath 40 can also engage with the main housing 32 at a more distal location, adjacent to the distal seal 42, such as with another O-ring type seal 45, to help guide the longitudinal motion of the shuttle sheath 40 within the main housing 32.

FIG. 4 shows the shuttle 22 in the distal position with the distal end of the sheath 40 projecting through the distal seal 42. As shown, the seal 42 separates in response to the distal motion of the shuttle sheath 40 and seals around the outer surfaces of the distal end 44 of the shuttle sheath.

Figure 2:
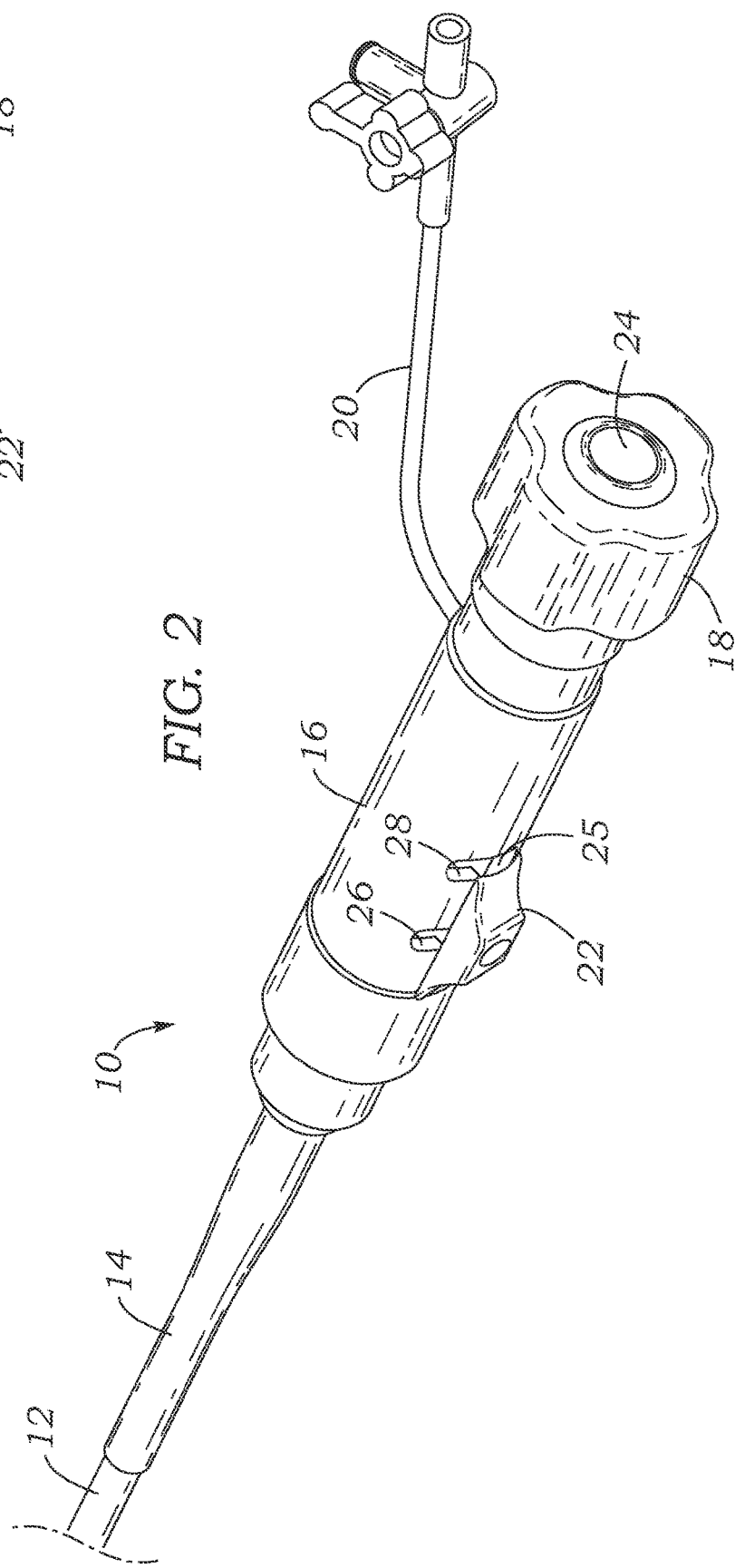
FIG. 2 is a perspective view of the device of FIG. 1.

The shuttle 22 further comprises an actuator 30 (see FIG. 3) that projects radially from the shuttle sheath 40 through a longitudinal slot 25 in the housing 16 (see FIG. 2). The actuator 30 can be used to manually move the shuttle 22 between the distal and proximal positions along the slot 25 in the housing 16. The actuator 30 can lock with the housing 16 to hold the shuttle 22 in the proximal position, such as by rotating and engaging the actuator 30 into a notch 28 extending circumferentially from the slot 25, and the actuator 30 can lock with the housing to hold the shuttle 22 in the distal position, such as by rotating and engaging the actuator 30 into a notch 26 extending circumferentially from the slot 25 (see notches 26, 28 in FIGS. 2 and 3).

The proximal hub 18 is coupled to the proximal end of the housing 16 such that the hub 18 can move longitudinally between a proximal position (FIGS. 1-5) and a distal position (FIG. 6), relative to the housing 16. The hub 18 houses the proximal seal 56 and, optionally, a secondary proximal seal 54, as shown in FIGS. 4-6. The hub 18 comprises a proximal port 24 of the introducer, through which a delivery catheter with a medical device mounted thereon can be inserted and removed. The hub 18 can be engaged with the proximal end of the housing 16 via corresponding helical ridges 60 and grooves 62 such that the hub 18 can be selectively moved between the proximal and distal positions by rotating the hub 18 relative to the housing 16, as best shown in FIGS. 5-6. The hub 18 and the housing 16 can also comprise inter-engaging features that hold or lock the hub in the distal position and/or in the proximal position. Sealing features, such as O-rings, can be positioned between the hub 18 and housing 16.

The housing 16 can include a proximal tube 52 that extends proximally from the larger diameter section 50 of the main housing 32. When the hub 18 is in the proximal position (FIGS. 1-5), a proximal end 53 of the tube 52 is distal to the proximal seals 54, 56, which allows the proximal seals to remain closed. When the hub 18 is in the distal position (FIG. 6), the proximal end 53 of the tube 52 extends through the proximal seals 54, 56, allowing a delivery catheter with a medical device mounted thereon to be inserted through the proximal port 24 and into the tube 52 or to be retracted from the tube 52 through the port 24.

FIG. 6 shows the hub 18 in the distal position with the proximal end 53 of the tube 52 projecting through the proximal seals 54, 56. As shown, the seals 54, 56 separate and open to permit the proximal end 53 of the tube 52 to extend therethrough and seal around the outer surfaces of the tube. As discussed in greater detail below, in the illustrated embodiment, the distal seal 42 and the proximal seal 56 provide zero and guidewire seals, while the proximal seal 54 provides an instrument seal, for example, with the delivery catheter. Other embodiments include different combinations and/or configurations of zero, guidewire, and instrument seals.

During an exemplary procedure, the distal sheath 12 can be initially inserted into the patient's vessel, for example, over a guidewire, with the shuttle 22 in the proximal position and the hub 18 in the proximal position, such that the distal seal 42 and the proximal seals 54, 56 are closed to reduce blood loss as shown in FIG. 5. As discussed in greater detail below, the distal seal 42 and proximal seal 56 seal around the guidewire, providing hemostasis in this state. In this position, the proximal end 48 of the shuttle sheath 40 is positioned adjacent to the distal end of the tube 52 to create a continuous conduit of substantially constant diameter. The hub 18 can then be moved to the distal position, as shown in FIG. 6, to open the proximal seals 54 and 56 and allow a delivery catheter to be inserted through the proximal port 24, through the tube 52, and into the shuttle sheath 40. Once the distal portion of the delivery catheter with the medical device mounted thereon is inserted past the proximal seals 54, 56 and into the tube 52, the hub 18 can be moved back proximally such that the proximal seals 54, 56 slide off of the tube 52 and the proximal seal 54 seals around the catheter. This configuration can allow the catheter to slide through the proximal seals 54, 56 as the catheter is advanced further while the proximal seal 54 maintains a tight seal around the catheter.

With the medical device of the delivery catheter positioned within the shuttle sheath 40, the shuttle 22 can be moved distally to its distal position (FIG. 4) such that the distal end 44 of the shuttle sheath forces open the distal seal 42. The delivery catheter can then be advanced distally from the shuttle sheath 40, through a distal section 46 of the housing 16, having a similar diameter to the shuttle sheath 40 in the illustrated embodiment, and through the sheaths 12, 14 into the patient's vasculature. Once the distal portion of the delivery catheter with the medical device mounted thereon is advanced past the distal seal 42, the shuttle 22 can be moved back to the proximal position (FIG. 5) such that the distal seal 42 slides off the shuttle sheath 40, which can allow the catheter to slide through the distal seal 42 as the catheter is advanced further and/or partially retracted.

The shuttle sheath 40 and the proximal tube 52 can comprise a sufficiently rigidity such that they do not collapse within the seals, and instead hold the seals open to allow passage of the medical device through the seals. The shuttle sheath 40 and tube 52 thus protect the medical device from being damaged by the seals and prevent the seals from snagging on the device and/or dislodging the device from the catheter. The inner surfaces of the shuttle sheath 40 and the tube 52 can be smooth to minimize friction with the medical device and to prevent damage to the device.

After a desired procedure is attempted using the delivery system within the body, the delivery catheter is retracted proximally through the introducer 10. In some cases, the medical device, e.g., a prosthetic heart valve, may have been successfully implanted in the heart and just the catheter is retracted. However, in other cases the medical device may be retracted still mounted on the catheter. For example, if the native aortic valve is heavily stenosed, a crimped prosthetic heart valve may not be able to cross through the aortic valve as needed for implantation thereof. Instead, the catheter and crimped valve can be retracted back into the introducer 10 and removed from the patient's body.

In such cases, the shuttle sheath 40 can be advanced distally through the distal seal 42 and the medical device can be guided back into the distal end 44 of the shuttle sheath 40. The shuttle 22 and the medical device can then be retracted back through the distal seal 42, into the housing 16 of the introducer 10. The distal seal 42 can continue to seal around the guidewire in this state. The proximal seals 54, 56 can then be opened by moving the hub 18 to the distal position, which permits the delivery catheter with medical device to be removed from the introducer 10 through the proximal port 24. In this way, the medical device can be retrieve back out of the body in a re-usable state since the introducer 10 eliminates or reduces the risk of damage to the medical device by the seals.

As the delivery catheter is retrieved, the introducer 10 can remain in the patient with the distal seal 42 maintaining hemostasis. In order to treat the aortic valve stenosis, for example, a balloon valvuloplasty procedure, or other procedure, can then be performed using the same introducer 10. After the aortic valve is treated, the same delivery catheter and medical device that was retrieved, or a new delivery system, can be re-introduced using the same introducer 10.

Figure 7:
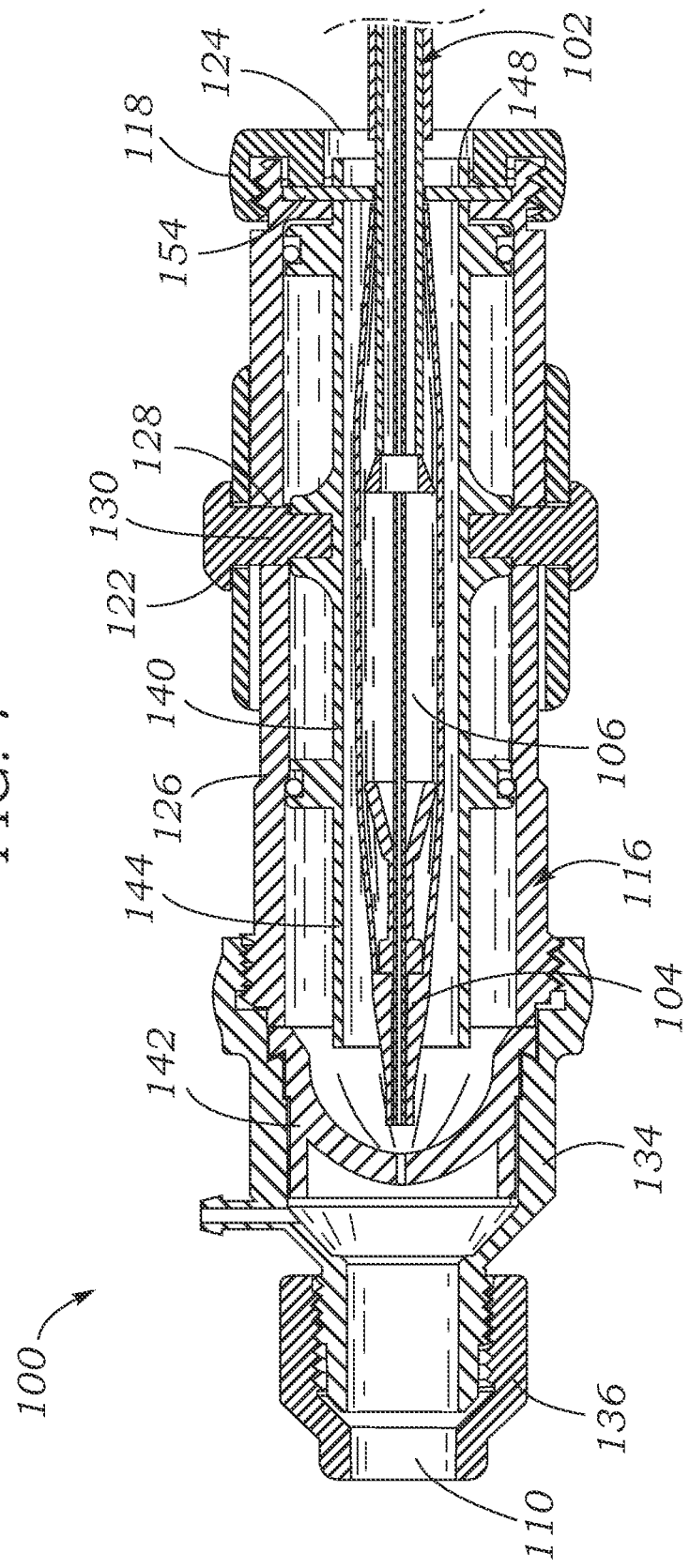
FIG. 7 is a cross-sectional view of another exemplary introducer device with a delivery catheter inserted into the introducer device.

FIG. 7 shows another exemplary introducer 100 that functions similarly to the introducer 10. The introducer 100 can comprise a housing 116 that comprises a main housing 126, a distal seal housing 134, and/or a distal sheath housing 136. A shuttle 122 is slidably mounted within the housing 116 and comprises a shuttle sheath 140 and actuator 130 that extends radially through a slot 128 in the housing 116. A distal seal 142 is housed within the distal seal housing 134, and a distal sheath 110 can be secured by the distal sheath housing 136. A proximal hub 118 can be secured to the proximal end of the housing 116 and can retain a proximal seal 154 adjacent to the proximal port 124 of the introducer 100.

Similar to as described above with reference to the introducer 10, the introducer 100 can allow a delivery system to be introduced into a patient's vasculature without using a protective loader device, and the introducer 100 can further allow the delivery system to be retrieved back out of the patient's body through the introducer without damage so that it can be reused.

To load a delivery system 102 into the introducer 100, the shuttle 122 is moved proximally so that a proximal end 148 of the shuttle sheath 140 pushes through and opens the proximal seal 154, as shown. After the medical device 106 is inserted through the proximal port 124 into the shuttle sheath 140, although not shown, the shuttle 122 can be moved distally such that the proximal seal 154 seals around the catheter 104 and the distal end 144 of the shuttle sheath 140 pushes open the distal seal 142. The delivery system 102 can then be advanced out of the distal end 144 of the shuttle sheath, through the distal sheath 110 and into the patient's body. The shuttle can then be moved to a neutral position such that both seals 142, 154 are free of the shuttle sheath 140, with the proximal seal 154 sealing around the catheter 104 during the procedure. The process can then be reversed to retrieve the delivery system back out of the patient's body, as described with the introducer 10. An alternative embodiment of the introducer 100 includes a distal instrument seal, which permits the shuttle 122 to be moved back to the proximal position with the proximal seal 154 remaining open during the subsequent procedure.

Figure 8:
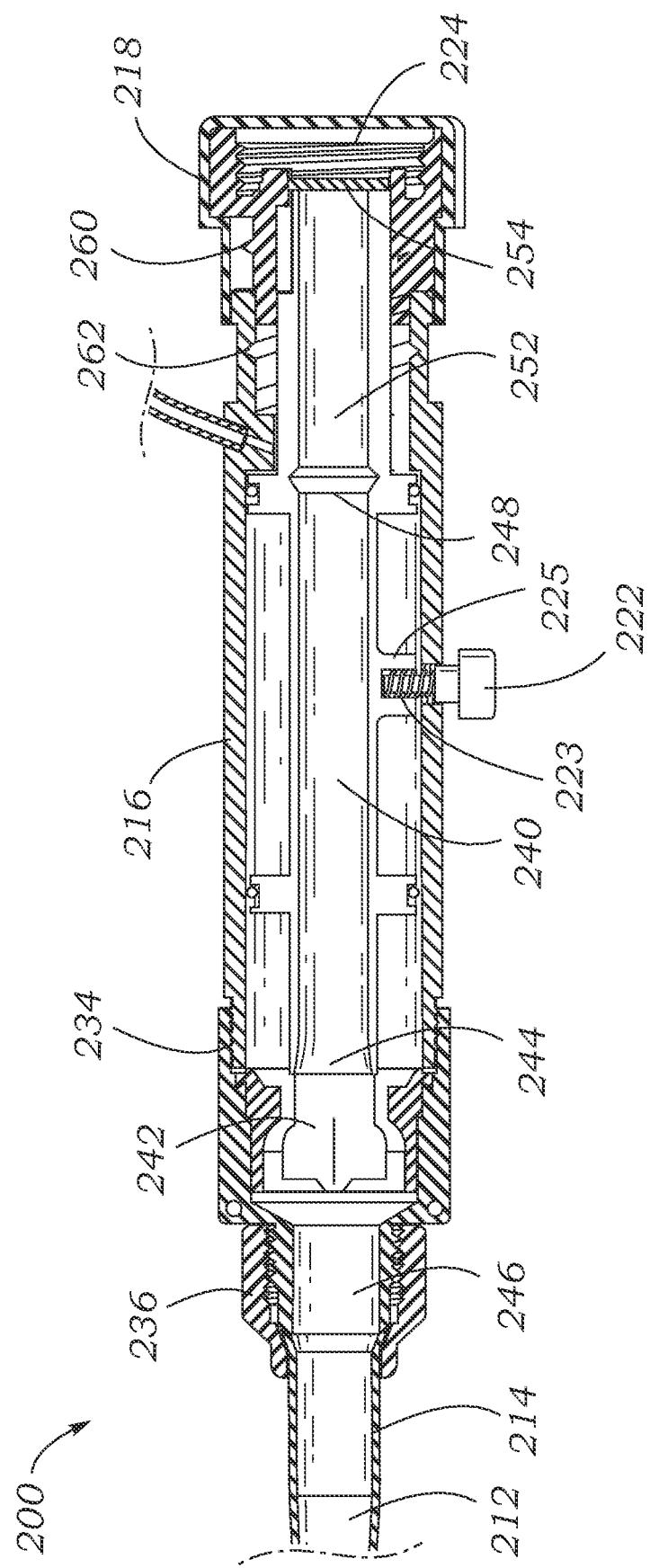
FIG. 8 is a cross-sectional view of another exemplary introducer device.

FIG. 8 shows another exemplary introducer 200 that functions similarly to the introducer 10. The introducer 200 can comprise a main housing 216, a distal seal housing 234, and a distal sheath housing 236. A shuttle 222 is slidably mounted within the main housing 216 and comprises a shuttle sheath 240 and an actuator 233 that extends radially through a slot 225 in the housing. A distal seal 242 can be housed within the distal seal housing 234 and distal sheaths 212, 214 can be secured by the distal sheath housing 236. A proximal hub 218 can be mounted to the proximal end of the main housing 216 and can retain a proximal seal 254 adjacent to the proximal port 224 of the introducer 200.

Similar to the embodiment described above with reference to the introducer 10, the introducer 200 can allow a delivery system to be introduced into a patient's vasculature without using a protective loader device, and the introducer 200 can further allow the delivery system to be retrieved back out of the patient's body through the introducer without damage so that it can be reused.

To load a delivery system into the introducer 200, the hub 218 is moved distally, such as by rotating the hub 218 relative to the main housing 216 about the respective helical threads 260, 262 so that a proximal end of a proximal tube 252 of the main housing pushes through and opens the proximal seal 254. The shuttle 222 can also be moved proximally toward the tube 252. After a medical device of the delivery system is inserted through the proximal port 224, through the proximal tube 252, and into the shuttle sheath 240, the hub 218 can be moved back proximally such that the proximal seal 254 moves off of the tube 252 and seals around a delivery catheter of the delivery system. The shuttle 222 can then be moved distally such that the distal end 244 of the shuttle sheath 240 pushes open the distal seal 242. The delivery system can then be advanced out of the distal end 244 of the shuttle sheath, through a distal chamber 246, through the distal sheaths 212, 214, and into the patient's body. The shuttle 222 can then be moved to the proximal position such that both seals 242, 254 can seal around the catheter. The process can then be reversed to retrieve the delivery system back out of the patient's body through the introducer 200, as described with the introducer 10.

Figure 9:
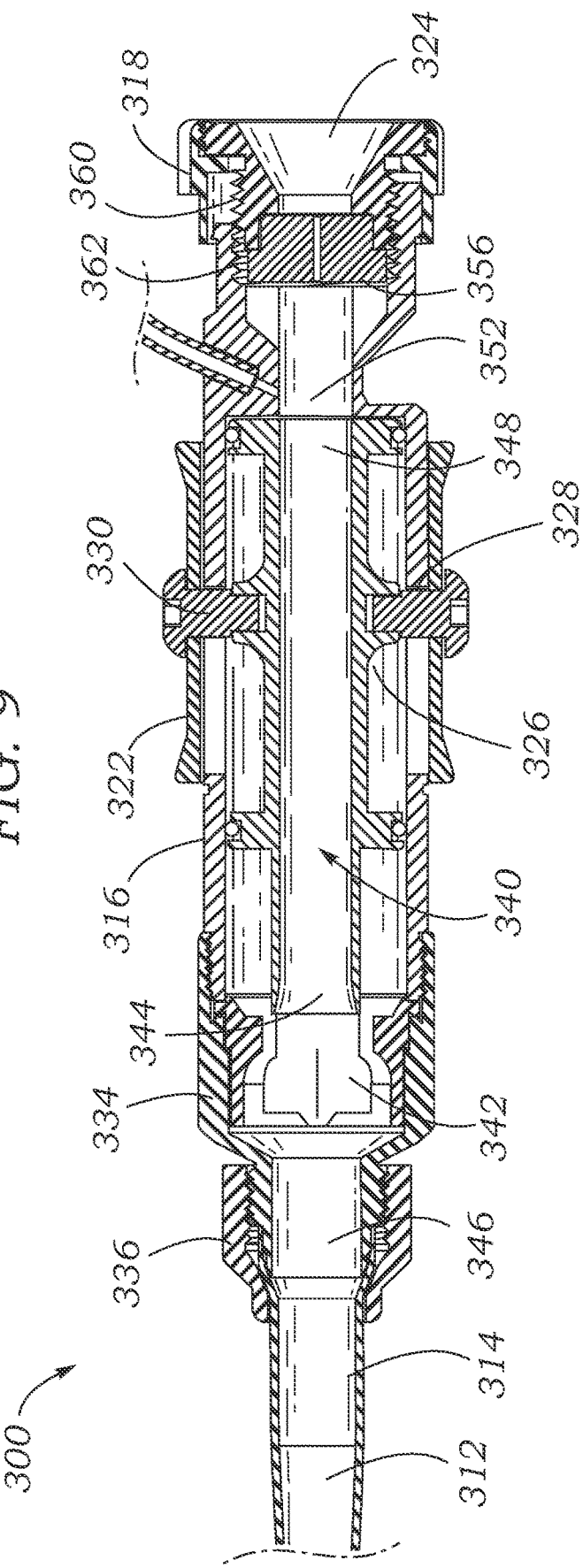
FIG. 9 is a cross-sectional view of another exemplary introducer device.

FIG. 9 shows another exemplary introducer 300 that functions similarly to the introducer 10. The introducer 300 can comprise a main housing 316, a distal seal housing 334, and a distal sheath housing 336. A shuttle 322 is slidably mounted to the main housing 316 and comprises a shuttle sheath 340 and an actuator 330 that extends radially through slots 326, 328 in the housing. A distal seal 342 can be housed within the distal seal housing 334 and distal sheaths 312, 314 can be secured by the distal sheath housing 336. A proximal hub 318 can be mounted to the proximal end of the main housing 316 and can retain a proximal seal 356 adjacent to the proximal port 324 of the introducer 300.

Similarly to the embodiment described above with reference to the introducer 10, the introducer 300 can allow a delivery system to be introduced into the patient's vasculature without using a protective loader device, and the introducer 300 can further allow the delivery system to be retrieved back out of the patient's body through the introducer without damage so that it can be reused.

To load a delivery system into the introducer 300, the hub 318 is moved distally, such as by rotating the hub 318 relative to the main housing 316 about the helical threads 360, 362 so that a proximal end of a proximal tube 352 of the main housing pushes through and opens the proximal seal 356. The shuttle 322 can also be moved proximally toward the tube 352. After a medical device mounted on the delivery catheter of the delivery system is inserted through the proximal port 324, through the proximal tube 352, and into the shuttle sheath 340, the hub 318 can be moved back proximally such that the proximal seal 356 moves off of the tube 352 and seals around delivery catheter. The shuttle 322 can then be moved distally such that the distal end 344 of the shuttle sheath pushes open the distal seal 342. The delivery system can then be advanced out of the distal end 344 of the shuttle sheath, through a distal chamber 346, through the distal sheaths 312, 314, and into the patient's body. The shuttle 322 can then be moved to the proximal position such that both seals 342, 356 can seal around the catheter. The process can then be reversed to retrieve the delivery system back out of the patient's body through the introducer 300, as described above with reference to the introducer 10.

FIGS. 10A-10F and FIGS. 11A-11G illustrate respective exemplary seals 64 and 80 that can be used with an introducer. The seals 64, 80 are each independently suitable as the distal and/or proximal seals of any of the exemplary introducer devices disclosed herein. The seals 64, 80 are each capable of hemostatically sealing around a guidewire (guidewire seal) and are also each capable of hemostatically sealing with no object passing through the seal (zero seal). To accomplish this dual-sealing capability, the seals 64, 80 each include a narrow guidewire passage and a small flap or flaps of material that cover the guidewire passage and that are flexible enough and conformable enough to close the guidewire passage when no guidewire is present and to open and seal around a guidewire when one is present.

Figure 10A:
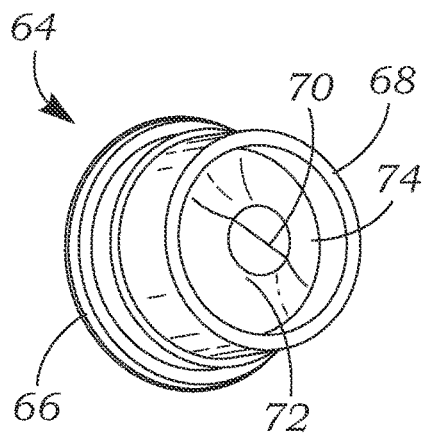
FIGS. 10A-10F are views of an exemplary hemostatic seal for an introducer device.
Figure 10B:
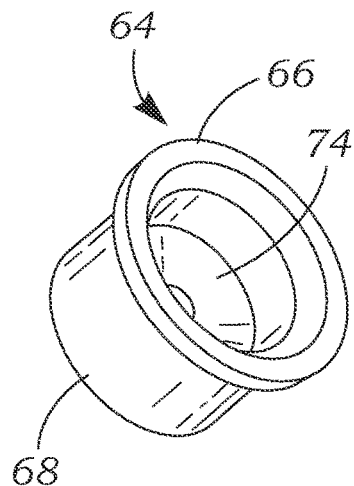
Figure 10C:
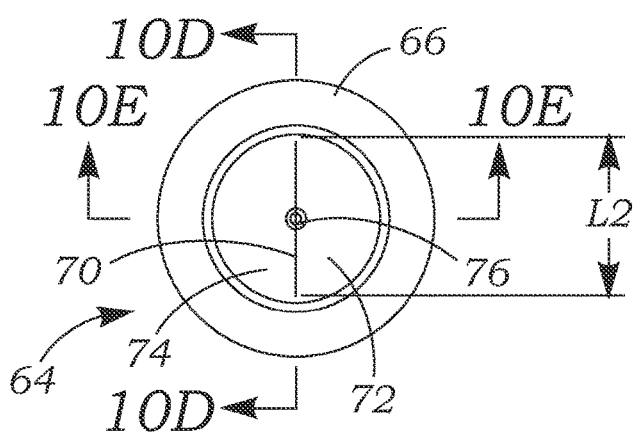
Figure 10D:
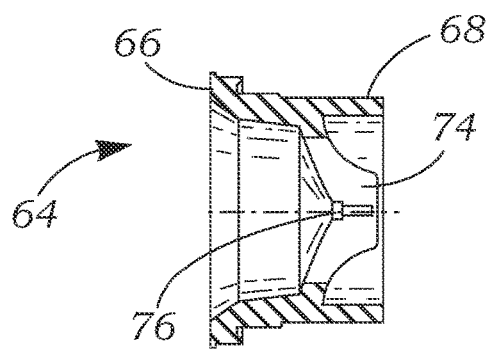
Figure 10E:
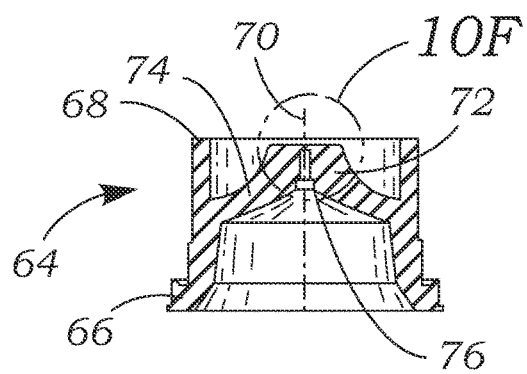
Figure 10F:
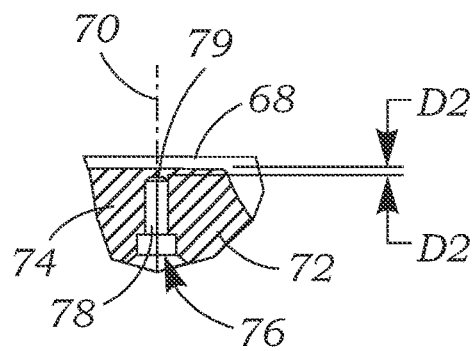

The seal 64 of FIGS. 10A-10F is a duckbill-type seal that comprises an annular body having a first end 66 (e.g., the proximal end) and a second end 68 (e.g., the distal end), and two semi-circular sealing members or lips 72, 74 that project radially inward from the annular body and meet along a generally linear slit 70. A narrow guidewire passage 76 is provided in the center of the slit 70 to allow a guidewire to extend through the slit without the rest of the slit having to separate, allowing the seal 64 to seal around a guidewire. As shown in FIG. 10F, the guidewire passage 76 can include a generally cylindrical portion 78 to seal around a guidewire and a flap or flaps 79 at the second end 68 of the seal that allows for coaptation of the lips 72, 74 even when no guidewire is present. In some embodiments, the length L2 (see FIG. 10C) of the slit 70 can be about 13 mm (about 0.5 inches), and the thickness D2 (see FIG. 10F) of the flap or flaps 79 can range from about 0.3 mm (about 0.012 inches) to about 0.5 mm (about 0.018 inches).

Figure 11A:
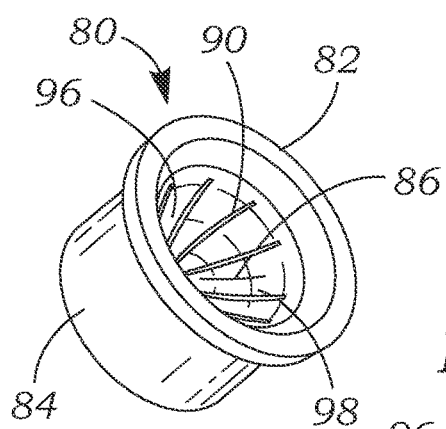
FIGS. 11A-11G are views of another exemplary hemostatic seal for an introducer device.
Figure 11B:
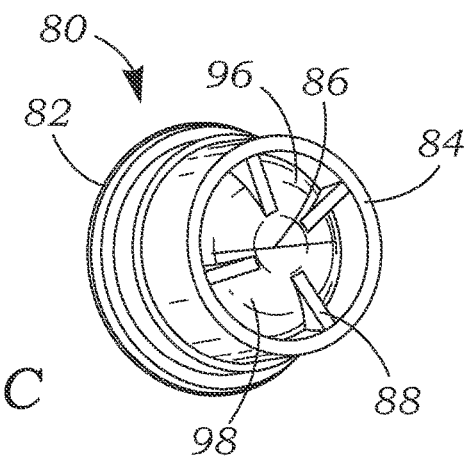
Figure 11C:
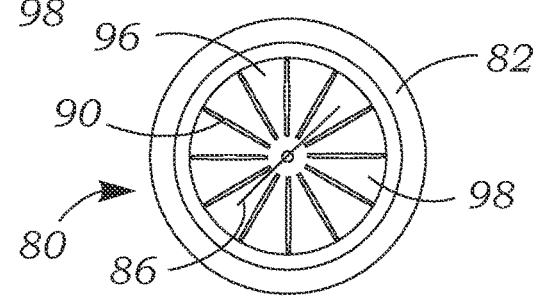
Figure 11D:
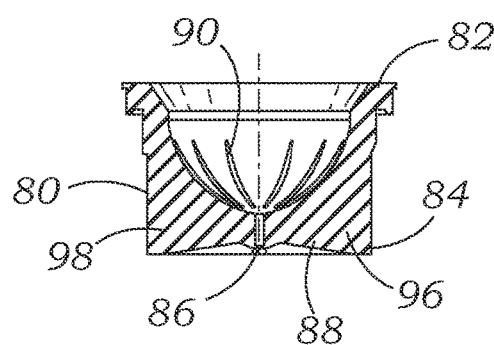
Figure 11E:
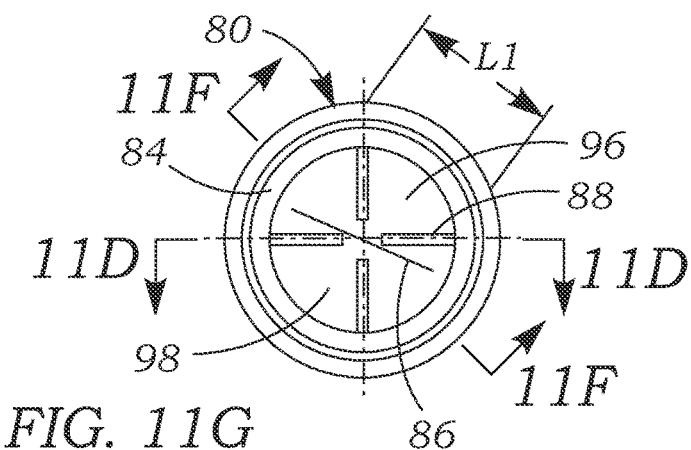
Figure 11F:
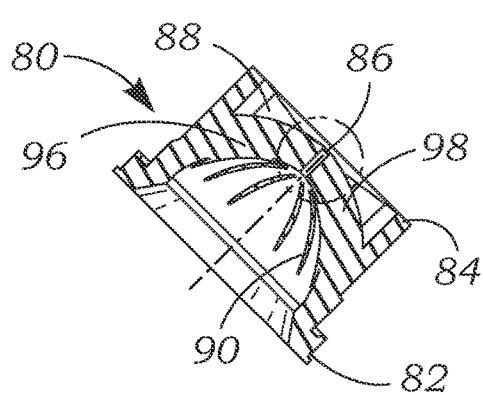
Figure 11G:
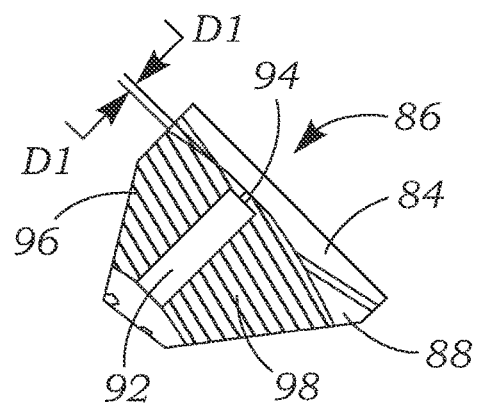
Figure 12:
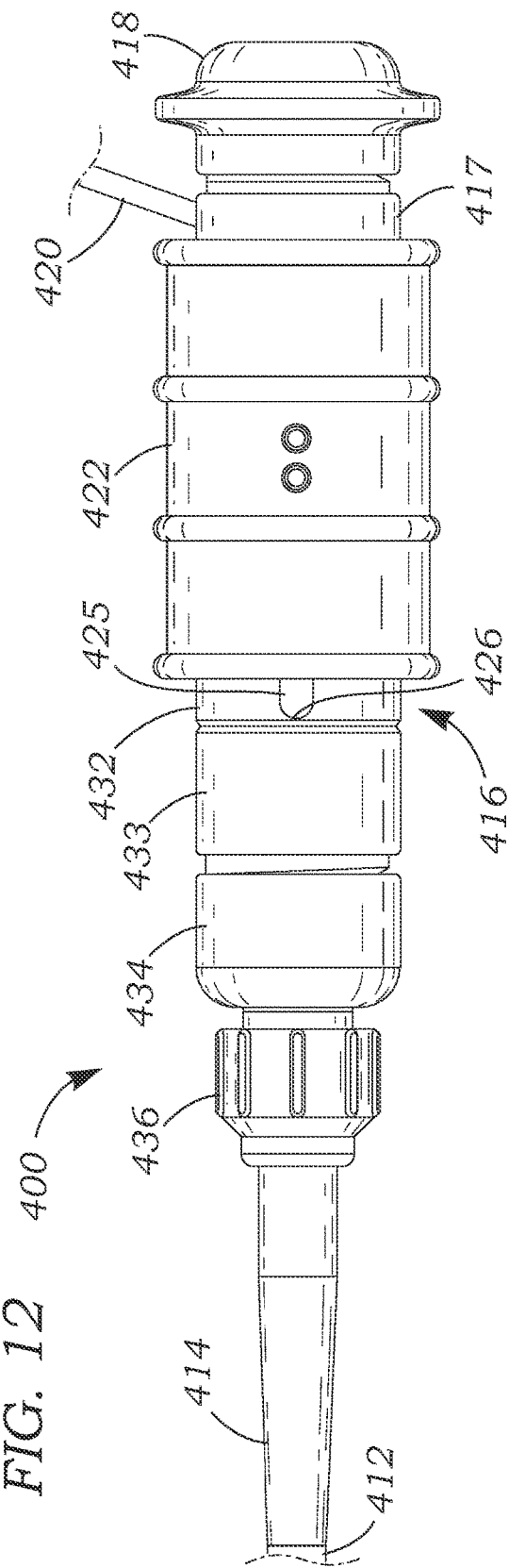
FIG. 12 is a side view of another exemplary introducer device.

The seal 80 of FIGS. 11A-11G is a dome-type seal that comprises an annular body having a first end 82 (e.g., the proximal end) and a second end 84 (e.g., the distal end), and two semi-circular sealing members or lips 96, 98 that project radially inward from the annular body and meet along a generally linear coaptation slit 86. Reinforcing struts 88 can be positioned on the second end 84 side of the lips 96, 98 (see FIGS. 11B and 11E), and/or ridges 90 can be positioned on the first side 82 of the lips 96, 98 (see FIGS. 11A and 11C). As shown in FIG. 11G, a narrow guidewire passage 92 is provided in the center of the coaptation slit 86 to allow a guidewire to extend through the slit 86 without the rest of the slit having to separate, allowing the seal 80 to seal around a guidewire. The guidewire passage 92 can seal around a guidewire when present, and a narrower/closed portion 94 of the passage 92, such as with a flap or flaps, at the second end 84 of the seal allows for full coaptation of the lips 98, 96 even when no guidewire is present in the guidewire passage 92. In some embodiments, the length L1 (see FIG. 11E) of the slit 86 can be about 13 mm (0.5 inches), and the thickness D1 (see FIG. 11G) of the flap or flaps 94 can range from about 0.3 mm (about 0.012 inches) to about 0.5 mm (about 0.018 inches).

Figure 13:
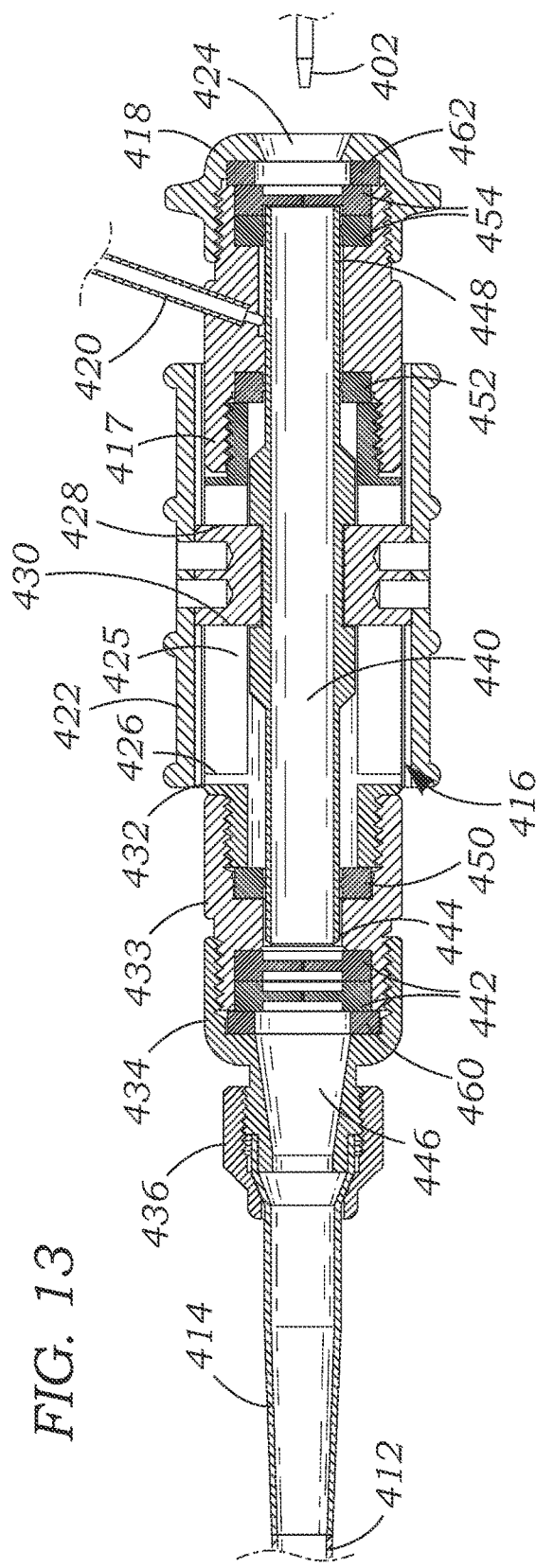
FIG. 13 is a cross-sectional view of the device of FIG. 12, showing the device's shuttle in a neutral position and a delivery catheter ready to be inserted.
Figure 14:
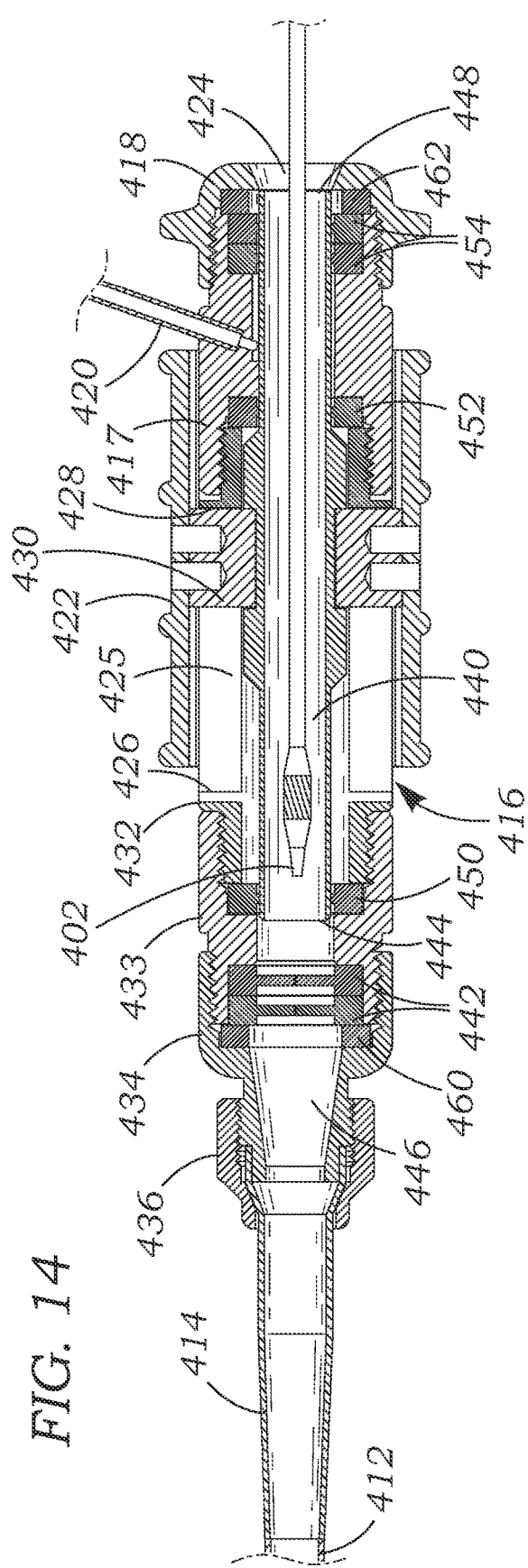
FIG. 14 is a cross-sectional view of the device of FIG. 12, showing the device's shuttle in a proximal position and the delivery catheter partially inserted into the device.
Figure 15:
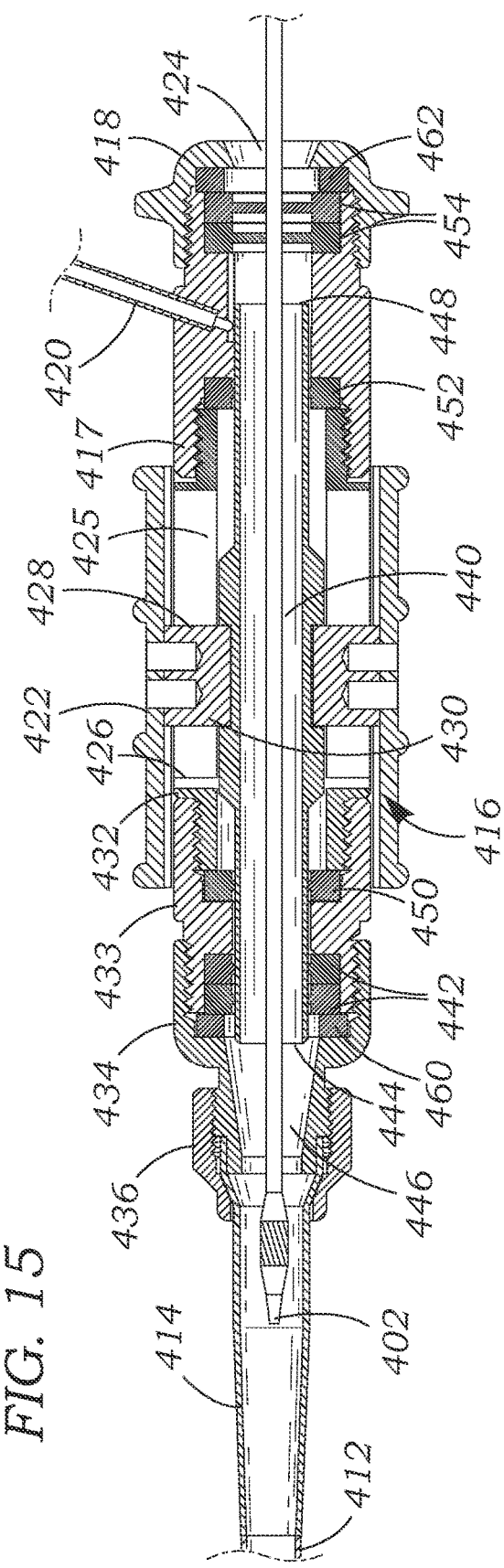
FIG. 15 is a cross-sectional view of the device of FIG. 12, with the device's shuttle in a distal position and the delivery catheter extending through the device.

FIGS. 12-15 show another exemplary introducer 400 that functions similarly to the introducer 10. As best shown in FIG. 13, the introducer 400 can comprise a housing 416 that comprises a main housing 432, a distal seal housing 433, one or more distal housing portions 434, 436, a proximal seal housing 417, and/or a proximal end housing 418. A flush port 420 can be coupled to the housing 416 at any point. A shuttle 422 is slidably mounted to the housing 416 and comprises a shuttle sheath 440 and actuator 430 that extends radially through a slot 425 in the housing, as best shown in FIG. 14. The shuttle can slide longitudinally between a proximal position where the actuator 430 abuts a proximal end 428 of the slot 425, and distal position wherein the actuator abuts a distal end 426 of the slot 425. More than one slot 425 and more than one actuator 430 can be included.

One or more distal seals 442 are housed within the distal seal housing 433, and an additional distal shuttle seal 450 can be mounted around the shuttle sheath 440 within the housing 416. Similarly, one or more proximal seals 454 are housed within the proximal seal housing 417, and an additional proximal shuttle seal 452 can be mounted around the shuttle sheath 440 within the housing 416. The distal seals 442 can be secured between the distal seal housing 433 and the distal housing portion 434 with an annular gasket 460. Similarly, the proximal seals 454 can be secured between the proximal seal housing 417 and the proximal end housing 418 with an annular gasket 462. Distal sheaths 412 and 414 can be secured to the introducer housing 434 by a distal sheath housing 436.

Similar to the embodiment described above with reference to the introducer 10, the introducer 400 can allow a delivery system to be introduced into a patient's vasculature without using a protective loader device, and the introducer 400 can further allow the delivery system to be retrieved back out of the patient's body through the introducer without damage so that it can be reused.

To load a delivery system 402 into the introducer 400, the shuttle 422 is moved proximally so that a proximal end 448 of the shuttle sheath pushes through and opens the proximal seals 454 (see FIG. 14). After the medical device mounted on the delivery catheter of the delivery system is inserted through the proximal port 424 into the shuttle sheath 440, the shuttle 422 can be moved distally such that the proximal seals 454 seal around the catheter and the distal end 444 of the shuttle sheath pushes open the distal seals 442 (see FIG. 15). The delivery system 402 can then be advanced out of the distal end 444 of the shuttle sheath, through a tapered transition 446, through the distal sheaths 414, 412 and into the patient's body. The shuttle 422 can then be moved to a neutral position such that the distal and proximal seals 442, 454 are free of the shuttle sheath 440 and can seal around the catheter (see FIG. 13), or alternatively the shuttle 422 can be moved back to the proximal position with the proximal seals 454 remaining open during the subsequent procedure. The process can then be reversed to retrieve the delivery system back out of the patient's body, as described with the introducer 10.

FIG. 16 shows exemplary introducer 500 that includes housing components that can be split apart along generally longitudinal seams. The introducer 500 can comprise a main housing 532 that splits apart into components 532A and 532B (as shown in FIG. 17), a distal housing 533 that splits apart into components 533A and 533B (as shown in FIG. 18), and a shuttle actuator 522 that splits into components 522A, 522B, 522C, and 522D (as shown in FIG. 19). The ability of these components to split apart can allow these components to be removed from around a catheter passing through the introducer into the patient's body, without having to slide the components proximally off the end of the catheter system. Other parts of the introducer 500, such as other components of the shuttle and proximal housing, can also be disassembled into smaller parts or otherwise configured to be removed from around the catheter. This can increase the working length of the catheter system by shortening the length of the remaining portion of the introducer that projects from the patient's body.

The introducer 500 can further comprise one or more additional distal housing portions such as 534, 536, a distal sheath 512, and/or a proximal housing 518. The shuttle actuator 522 is slidably mounted with the housing slots 525A, 525B (see FIG. 17) and can comprises a shuttle sheath within the housing that slides longitudinally with the actuator 522 between a proximal position where one or more proximal seals are opened and a distal position where one or more distal seals are opened, as described for other embodiments of introducers disclosed herein.

With the delivery catheter inserted through the introducer into the patient's body, the disassembleable components 522, 532, 533 and/or other components of the introducer 500 can be split apart and removed laterally from the catheter, leaving the seals and the distal-most portions of the introducer (e.g., 512, 534, 536) engaged with the catheter and patient for hemostatic sealing purposes. The catheter can then be inserted further distally into the patient, as needed, due the reduced length thereof disposed within the introducer 500. After the catheter-based procedure is completed, components of the introducer 500 removed to increase the working length of the catheter can optionally be reassembled around the catheter to restore partial or full functionality of the introducer. Alternatively, the delivery catheter can simply be retracted out of the body through the remaining distal portions of the introducer 500 without reassembly of the removed components.

FIGS. 20-23 show another exemplary introducer 600 that includes telescoping housing components that allow the housing of the introducer 600 to shorten and to lengthen to load a delivery catheter through the distal seal thereof. The introducer 600 includes an outer housing 604, an intermediate housing 602, an inner distal housing 606, a proximal housing 608, a proximal end portion 610, a distal sheath 612, a distal sheath housing 616, an inner sheath 618 (FIG. 21), lateral ports 620, 622 (FIG. 20), and/or a proximal port 624. A distal seal is housed in the inner distal housing 606, and a proximal seal is housed in the proximal housing 608.

Figure 20:
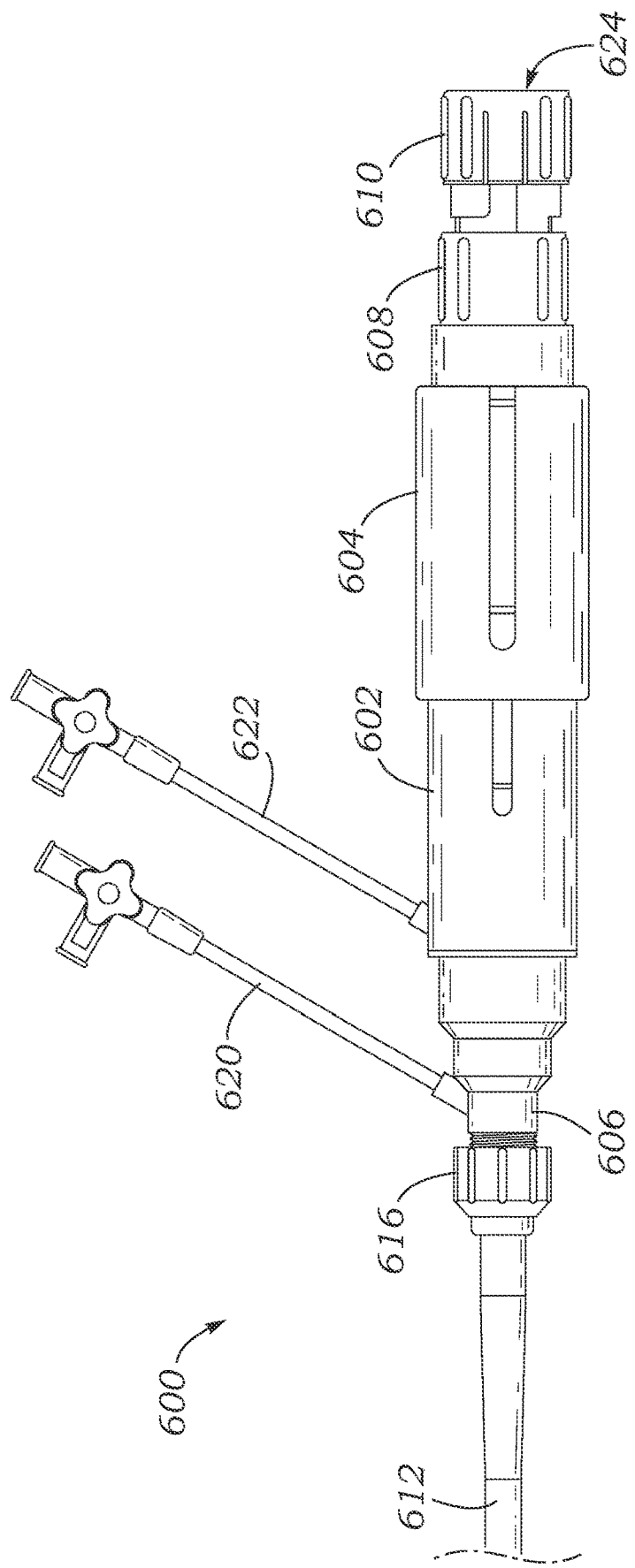
FIG. 20 is a side view of another exemplary embodiment of an introducer device, with a telescoping proximal body.
Figure 21:
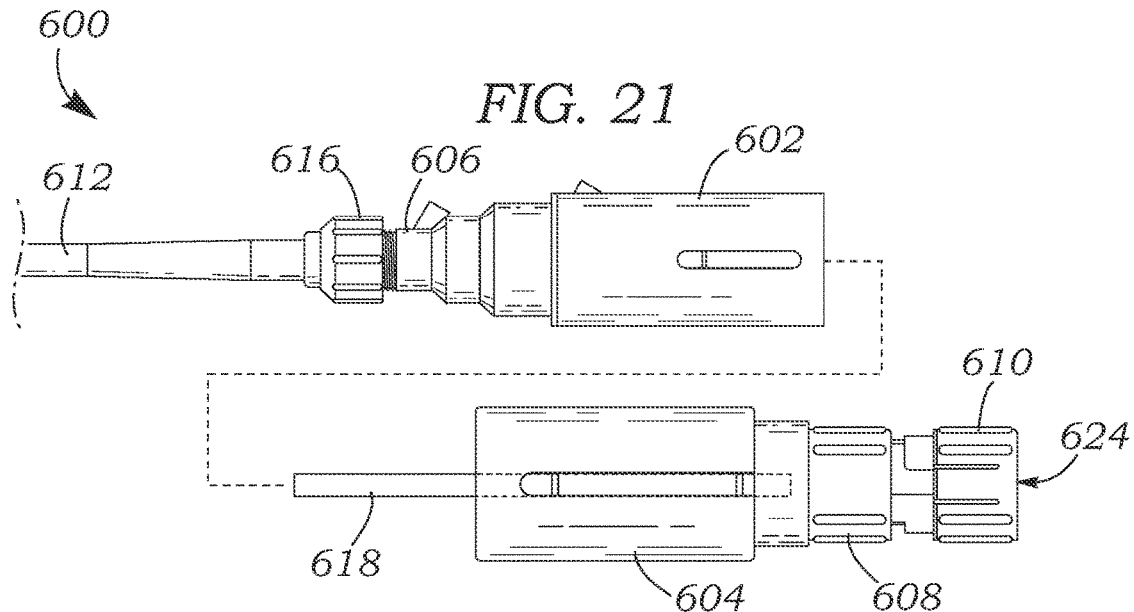
FIG. 21 is a side view of the device shown in FIG. 20, with the proximal body separated into two sections.
Figure 22:
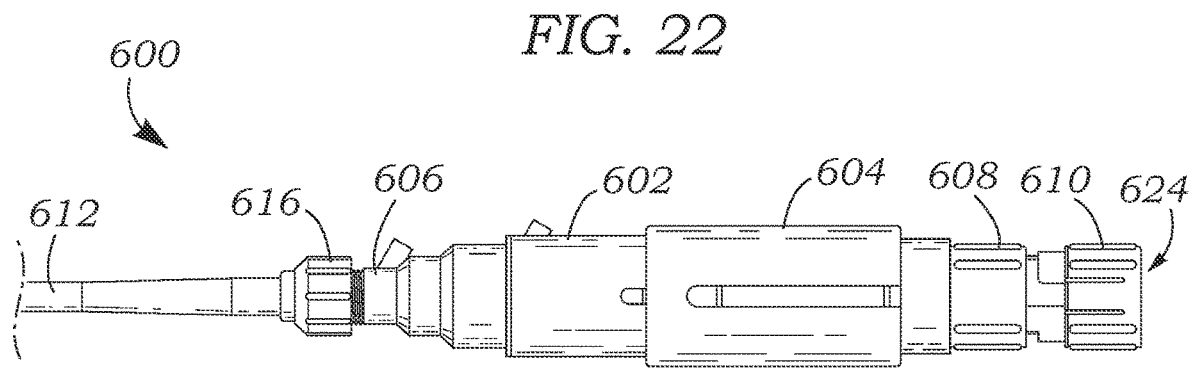
FIG. 22 is a side view of the device shown in FIG. 20, with the proximal body assembled and in an elongated configuration.
Figure 23:
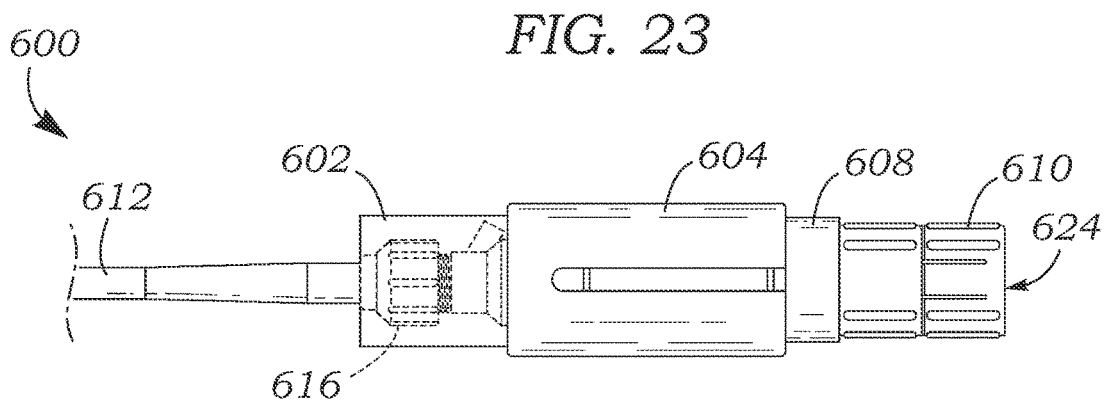
FIG. 23 is a side view of the embodiment of FIG. 20, with the proximal body in a shortened configuration.
Figure 26:
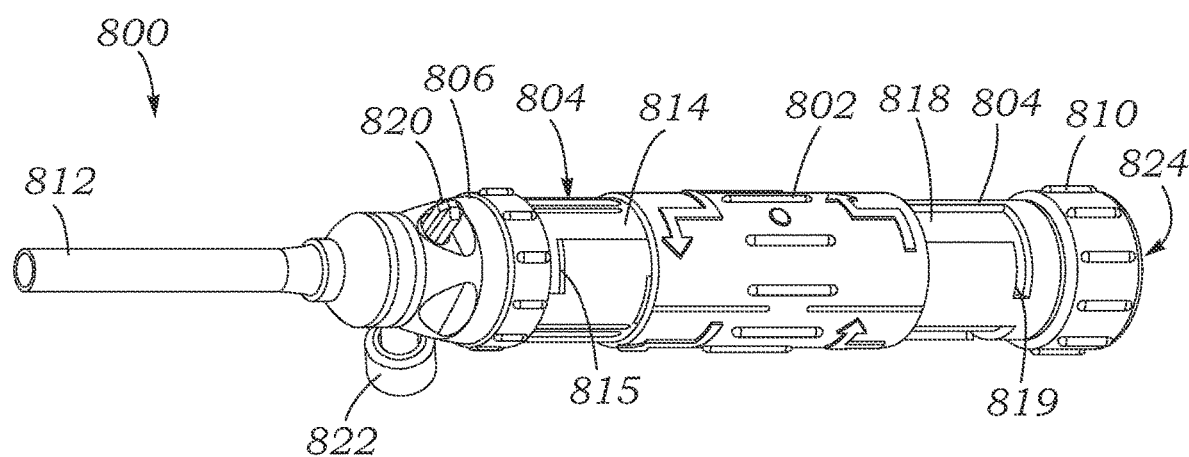
FIG. 26 is a perspective view of another exemplary embodiment of an introducer device.
Figure 27:
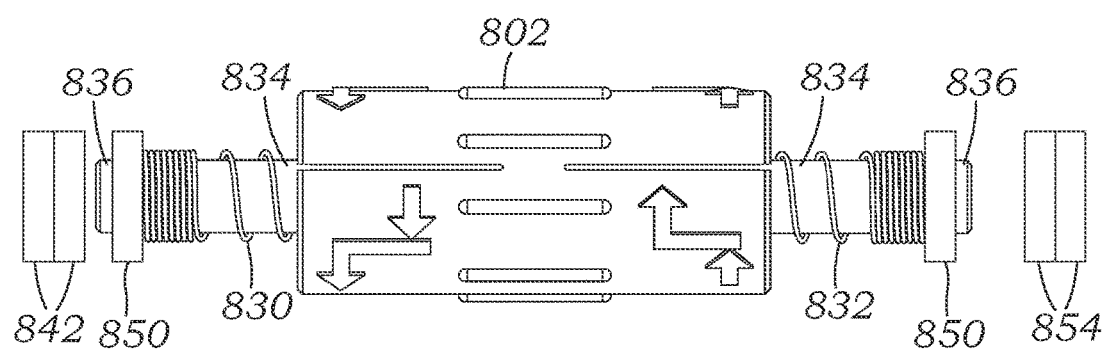
FIG. 27 is a side view of a shuttle portion of the device of FIG. 26.
Figure 30:
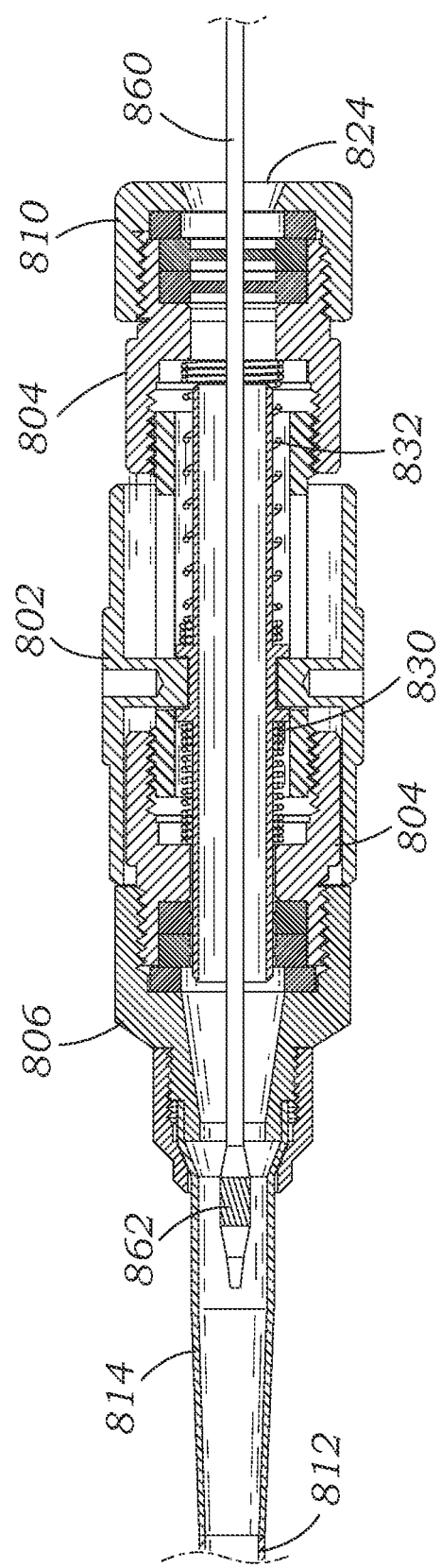
FIG. 30 is a cross-sectional view of the device of FIG. 26, with the proximal seal closed and a distal seal open, with the delivery catheter extending through the device.

A proximal portion of the introducer 600, including the outer housing 604 and proximal housing 608 (see right side of FIG. 20), can be telescopically moved distally over a distal portion of the introducer, including the intermediate housing 602 and inner distal housing 606 (see left side of FIG. 20). In addition, or alternatively, the intermediate housing 602 can be moved telescopically over the inner distal housing 606 and/or the sheath housing 616 (as shown in FIG. 23) to shorten the introducer 600. As the proximal portions of the device move over the distal portions of the device, the inner sheath 618 pushes through and opens the distal seal to allow a delivery catheter to be inserted into, and removed from, the patient without damage from the distal seal.

In addition, the proximal end portion 610 can be moved distally relative to the proximal housing 608 to cause an inner tube to push through and open the proximal seal, such that a delivery catheter can be inserted through the proximal port 624 and the proximal seal into the inner sheath 618, and also removed out of the inner sheath, without damage from the proximal seal. The interface between the proximal housing 608 and the proximal end portion 610 can comprise a push-to-lock type mechanism or a twist-to-lock type mechanism that allows the proximal seal to be selectively locked open and locked closed.

FIGS. 24-25 show another exemplary introducer 700 that includes telescoping housing components that allow the housing of the introducer to shorten and to lengthen to load a delivery catheter through the distal seal. The introducer 700 includes an outer housing 702, an inner housing 704, a distal seal housing 706, a proximal seal housing 708, a proximal end portion 710, a distal sheath 712, lateral ports 720, 722, and/or a proximal port 724. A distal seal is housed in the distal seal housing 706, and a proximal seal is housed in the proximal seal housing 708.

A proximal portion of the introducer 700, including the outer housing 702, can be telescopically moved distally over a distal portion of the introducer, including the inner housing 704, which shortens the introducer 700. As the outer housing 702 moves over the inner housing 704, an inner sheath attached to the outer housing 702 pushes through and opens the distal seal to allow a delivery catheter and medical device mounted thereon to be inserted into, and/or removed from, a patient without damage thereto from the distal seal. The introducer 700 can further comprise a spring 730 or other biasing mechanism within the housing that biases the outer housing 702 and inner sheath backwards, proximally away from the inner housing 704 and the distal seal. A user can move the outer housing 702 from the position shown in FIG. 24 to the position shown in FIG. 25 to open the distal seal and move the delivery catheter through the distal seal and then simply release the housing to allow the spring 730 to push the inner and outer housings 702, 704 back apart from each other to the position shown in FIG. 24, thereby closing the distal seal again. The inner and outer housings 702, 704 can also include a twist-to-lock mechanism that allows the introducer to be locked in the shortened configuration of FIG. 25 with the distal seal open, by twisting the outer housing 702 relative to the inner housing 704. Some embodiments of a twist-to-lock mechanism include mating threads on the inner and outer housings 702, 704, a bayonet mechanism, or the like.

In addition, the proximal end portion 710 can be moved distally relative to the proximal seal housing 708 to cause an inner tube to push through and open the proximal seal, permitting insertion of a delivery system through the proximal port 724 and the proximal seal into the inner sheath, and also removal out of the inner sheath, without damage thereto from the proximal seal. The interface between the proximal housing 708 and the proximal end portion 710 can comprise a push-to-lock type mechanism or a twist-to-lock type mechanism that allows the proximal seal to be selectively locked open and locked closed.

FIGS. 26-30 show an exemplary introducer 800 that includes a shuttle 802 that moves longitudinally relative to the rest of the introducer to open and close distal and proximal seals. The introducer 800 includes the shuttle 802, a main housing 804, a distal seal housing 806, a proximal end portion 810, a distal sheath 812, lateral ports 820, 822, and/or a proximal port 824. One or more distal seals 842 are housed in the distal seal housing 806, and one or more proximal seals 854 are housed in the proximal end portion 810 (see FIG. 27).

The shuttle 802 comprises an outer cylindrical portion that slides over the main housing 804 (FIG. 26) and a shuttle sheath 834 (FIG. 27) within the main housing. A distal end 836 of the shuttle sheath can push through and open the distal seals 842 when the shuttle 802 is moved to a distal position (FIG. 30), and the proximal end 838 of the shuttle sheath can push through and open the proximal seals 854 when the shuttle 802 is moved to a proximal position (FIG. 29). The shuttle sheath 834 can also be in an intermediate or neutral position (FIGS. 26-28), where both the distal and proximal seals 842, 854 are closed. Additional distal and proximal seals, such as O-rings 850, 852, can be positioned around the shuttle sheath 834 to seal against the inside of the main housing 804.

The introducer 800 can further comprise springs 830, 832 (FIG. 27) or other biasing mechanisms within the main housing 804 that bias the shuttle 802 toward the neutral position. One end of each spring 830, 832 can contact a respective O-ring 850, 852, while an opposite end of each spring contacts the shuttle 802. A user can move the shuttle 802 from the neutral position in FIGS. 26-28 in a proximal direction to open the proximal seals 854 (FIG. 29) in order to load a delivery catheter 860 with a medical device 862 mounted thereon into the shuttle sheath 834. The user can then release the shuttle 802 and/or move it distally with the help of the springs 830, 832 to the neutral position, such that the proximal seals 854 seal around the catheter 860 behind the medical device 862. Then the user can move the shuttle 802 to the distal position (FIG. 30) to open the distal seals 842 and move the delivery catheter 860 through the distal seals. After the medical device 862 mounted on the delivery catheter is moved distally past the distal seals 842, the user can release the shuttle 802 or move it proximally with the help of the springs 830, 832 to move the shuttle 802 back to the neutral position, thereby closing the distal seal around the catheter 860 as it is advanced into a patient.

The main housing 804 can comprise a longitudinal slots 814, 818 (FIG. 26) that allow the shuttle 802 to move longitudinally between the proximal and distal positions. In some embodiments, the main housing 804 can also include a distal slot 815 extending circumferentially from the longitudinal slot 814 to allow the shuttle 802 in the distal position to rotate relative to the main housing to lock the shuttle in the distal position with distal seals 842 open. Similarly, the main housing 804 can also include a proximal slot 819 extending circumferentially from the longitudinal slot 818 to allow the shuttle 802 in the proximal position to rotate relative to the main housing to lock the shuttle in the proximal position with proximal seals 854 open. The main housing 804 can also comprise one or more additional slots to allow the shuttle 802 to rotate to a locked position relative to the main housing in the neutral position.

Figure 31:
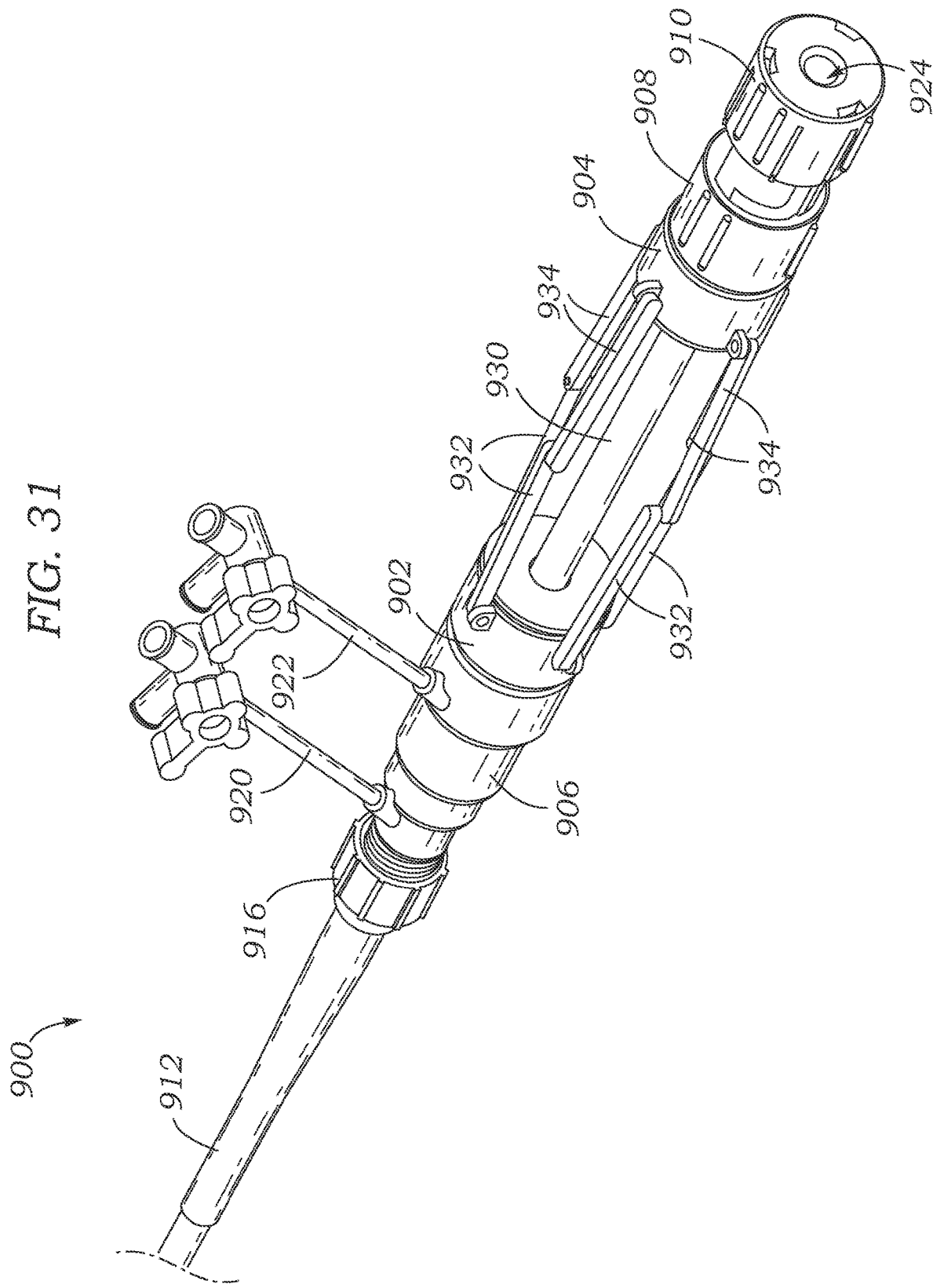
FIG. 31 is a perspective view of another exemplary embodiment of an introducer device that includes a hinge mechanism.
Figure 32:
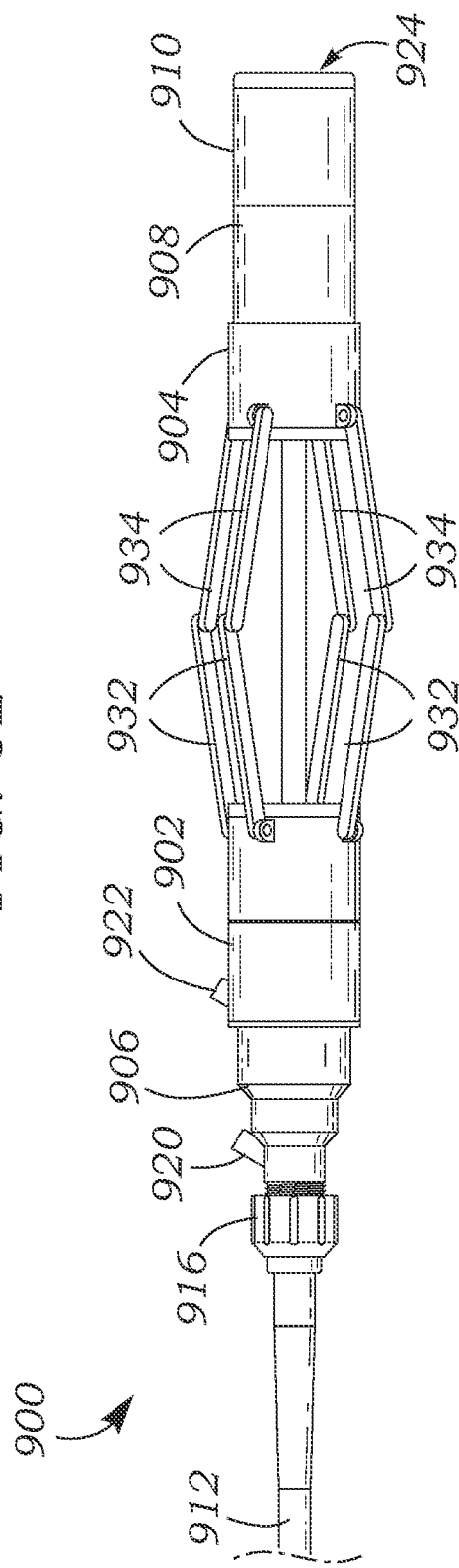
FIG. 32 is a side view of the device shown in FIG. 31, with the device in an elongated configuration.
Figure 33:
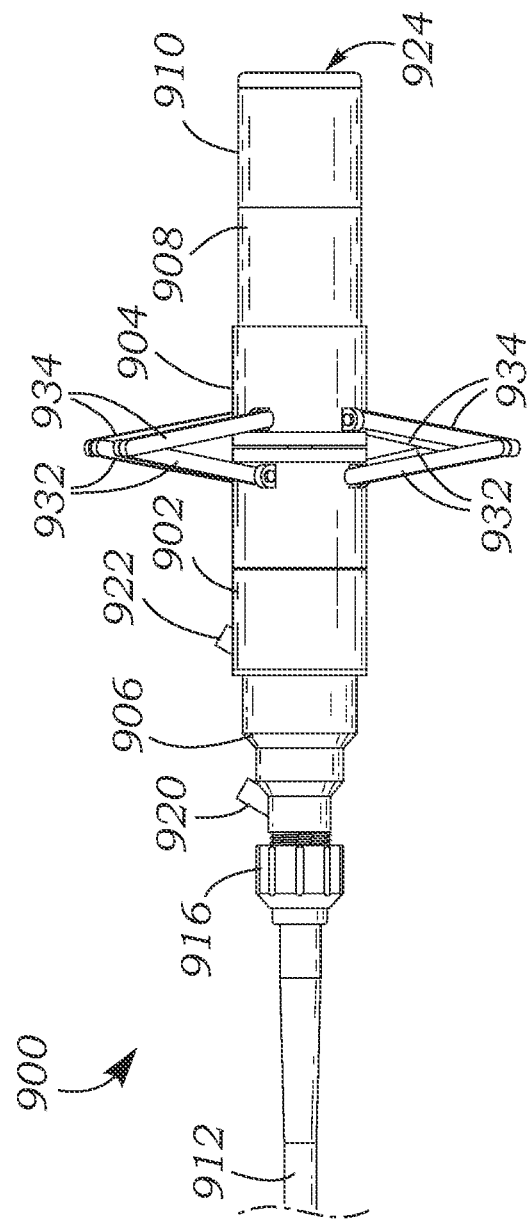
FIG. 33 is a side view of the device shown in FIG. 31, with the device in a shortened configuration.

FIGS. 31-33 show an exemplary introducer 900 that utilizes a hinge mechanism to allow distal and proximal portions of the introducer to move together and apart from each other to load a delivery catheter and device mounted thereon. The introducer 900 can include a distal housing 902, proximal housing 904, distal seal housing 906, proximal seal housing 908, proximal end portion 910, distal sheath 912, distal sheath housing 916, lateral ports 920, 922, proximal port 924, inner loader sheath 930, distal hinge arms 932, and/or proximal hinge arms 934. The hinge arms 932, 934 couple the distal housing 902 to the proximal housing 904 and allow the proximal portion of the introducer 900 to move between the proximal, expanded position shown in FIG. 32 and the distal, compressed position shown in FIG. 33. Any number of hinge arms 932, 934 can be included, such as four pairs of hinge arms, as illustrated, spaced at about 90° intervals around the housing.

The proximal end portion 910 can be engaged with the proximal seal housing 908 such that pushing the end portion 910 toward the proximal seal housing 908 forces an inner tube (such as the proximal end of the loader sheath 930) through a proximal seal and allows a delivery catheter and device to be inserted through the proximal port 924, through the proximal seal, and into the loader sheath 930. Once a medical device mounted on the catheter is advanced past the proximal sheath, the proximal end portion 910 can be moved back proximally to allow the proximal seal to seal around a portion of the catheter behind the mounted medical device.

With the delivery catheter loaded in the loader sheath 930, the proximal housing 904 can be moved distally relative to the distal housing 902, causing the hinge arms 932, 934 to flex and project radially outwardly, as shown in FIG. 33, while the loader sheath 930 moves distally through the distal seal housing 906 and opens the distal seal. With the loader sheath 930 positioned through the distal seal, the delivery catheter can be advanced through the distal sheath 912 and into a patient's body. The delivery catheter and device can also be retrieved back out of the patient's body by reversing this process without damage thereto from the seals.

While many different embodiments of introducer are individually described herein, any of the features, properties, and related methods of use that are described in relation to any one or more of these embodiments can also be included, used, or applied in an analogous manner with any other embodiments described herein, to the extent practicable.

As used herein, the terms "distal" and "distally" refer to a location or direction that is, or a portion of an elongated device that when implanted or inserted into a patient's vasculature (for example percutaneous insertion into a blood vessel) is farther away from an end of the device the projects from the body, and is closer toward the end of the device that is within the body. The terms "proximal" and "proximally" refer to a location or direction that is, or a portion of an elongated device that when implanted or inserted into a patient's vasculature (for example percutaneous insertion into a blood vessel) is closer toward an end of the device the projects from the body, and is farther from the end of the device that is within the body. The term "longitudinal" refers to the axis extending in the distal and proximal directions, or to the longitudinal axis of a cylindrical body or lumen.

For purposes of this description, certain aspects, advantages, and novel features of the embodiments of this disclosure are described herein. The disclosed methods, apparatuses, and systems should not be construed as limiting in any way. Instead, the present disclosure is directed toward all novel and nonobvious features and aspects of the various disclosed embodiments, alone and in various combinations and sub-combinations with one another. The methods, apparatuses, and systems are not limited to any specific aspect or feature or combination thereof, nor do the disclosed embodiments require that any one or more specific advantages be present or problems be solved.

Although the operations of some of the disclosed methods are described in a particular, sequential order for convenient presentation, it should be understood that this manner of description encompasses rearrangement, unless a particular ordering is required by specific language. For example, operations described sequentially may in some cases be rearranged or performed concurrently. Moreover, for the sake of simplicity, the attached figures may not show the various ways in which the disclosed methods can be used in conjunction with other methods.

As used herein, the terms "a", "an" and "at least one" encompass one or more of the specified element. That is, if two of a particular element are present, one of these elements is also present and thus "an" element is present. The terms "a plurality of" and "plural" mean two or more of the specified element. As used herein, the term "and/or" used between the last two of a list of elements means any one or more of the listed elements. For example, the phrase "A, B, and/or C" means "A," "B," "C," "A and B," "A and C," "B and C" or "A, B and C." As used herein, the term "coupled" generally means physically coupled or linked and does not exclude the presence of intermediate elements between the coupled items absent specific contrary language.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

The invention claimed is:

1. A device for introducing a catheter into a patient's vasculature, the device comprising:
   a housing;
   a distal sheath positioned distal to the housing and adapted to be inserted into a patient's vasculature with the housing positioned outside of the patient's vasculature;
   a hemostatic seal mounted within the housing;
   a shuttle comprising a tube positioned within the housing and movable longitudinally relative to the hemostatic seal between a proximal position and a distal position, wherein in the proximal position a distal end of the tube is positioned proximal to the hemostatic seal with the hemostatic seal closed, and wherein in the distal position the distal end of the tube extends through the hemostatic seal;

a spring positioned between the shuttle and the housing, wherein the spring is compressed when the tube is in the distal position and the spring biases the shuttle proximally relative to the housing and the hemostatic seal from the distal position toward the proximal position; and the shuttle further comprising an actuator coupled to the tube, wherein the actuator is positioned around and slides over the housing to allow a user to move the tube between the proximal and distal positions.

2. The device of claim 1, wherein the actuator comprises an outer cylindrical portion that slides over the housing.

3. The device of claim 1, wherein the spring is positioned around the tube.

4. The device of claim 1, wherein the shuttle is lockable relative to the housing with the tube in the distal position.

5. The device of claim 1, wherein the hemostatic seal comprises a narrow guidewire passageway adapted to hemostatically seal around a guidewire extending through the seal and comprises a flap or flaps adjacent to the guidewire passageway adapted to hemostatically seal when nothing is extending through the seal.

6. A device for introducing a catheter into a patient's vasculature, the device comprising:

a housing;

a distal sheath positioned distal to the housing and adapted to be inserted into a patient's vasculature with the housing positioned outside of the patient's vasculature;

a hemostatic seal mounted within the housing;

a shuttle comprising a tube positioned within the housing and movable longitudinally relative to the hemostatic seal between a proximal position and a distal position, wherein in the proximal position a distal end of the tube is positioned proximal to the hemostatic seal with the hemostatic seal closed, and wherein in the distal position the distal end of the tube extends through the hemostatic seal;

a spring positioned between the shuttle and the housing, wherein the spring is compressed when the tube is in the distal position and the spring biases the shuttle proximally relative to the housing and the hemostatic seal from the distal position toward the proximal position; and the shuttle further comprising an actuator coupled to the tube to allow a user to move the tube between the proximal and distal positions, wherein the actuator comprises an outer cylindrical portion that slides over the housing.

7. The device of claim 6, wherein the shuttle is lockable relative to the housing with the tube in the distal position.

8. The device of claim 6, wherein the spring is positioned around the tube.

9. The device of claim 6, wherein the hemostatic seal comprises a narrow guidewire passageway adapted to hemostatically seal around a guidewire extending through the seal and comprises a flap or flaps adjacent to the guidewire passageway adapted to hemostatically seal when nothing is extending through the seal.

10. The device of claim 6, wherein the actuator comprises a radial portion connected to the outer cylindrical portion and the tube, wherein the radial portion extends through a slot within a sidewall of the housing.

11. A device for introducing a catheter into a patient's vasculature, the device comprising:

a housing;

a distal sheath positioned distal to the housing and adapted to be inserted into a patient's vasculature with the housing positioned outside of the patient's vasculature;

a hemostatic seal mounted within the housing;

a shuttle comprising a tube positioned within the housing and movable longitudinally relative to the hemostatic seal between a proximal position and a distal position, wherein in the proximal position a distal end of the tube is positioned proximal to the hemostatic seal with the hemostatic seal closed, and wherein in the distal position the distal end of the tube extends through the hemostatic seal;

a spring positioned between the shuttle and the housing, wherein the spring is compressed when the tube is in the distal position and the spring biases the shuttle proximally relative to the housing and the hemostatic seal from the distal position toward the proximal position; and wherein the shuttle is lockable relative to the housing with the tube in the distal position.

12. The delivery device of claim 11, wherein the spring is positioned around the tube.

13. The delivery device of claim 11, wherein the hemostatic seal comprises a narrow guidewire passageway adapted to hemostatically seal around a guidewire extending through the seal and comprises a flap or flaps adjacent to the guidewire passageway adapted to hemostatically seal when nothing is extending through the seal.

14. The delivery device of claim 11, wherein the shuttle further comprises an actuator with a radial portion connected to the tube, wherein the radial portion extends through a slot within a sidewall of the housing.

15. The delivery device of claim 14, wherein the housing comprises a circumferential notch extending from the slot for locking the shuttle relative to the housing.

* * * * *